United States Patent
Miller et al.

(10) Patent No.: US 7,399,623 B2
(45) Date of Patent: Jul. 15, 2008

(54) MODIFIED FORMS OF PULLULANASE

(75) Inventors: Brian S. Miller, Burlingame, CA (US); Jayarama K. Shetty, Pleasanton, CA (US)

(73) Assignee: Genencor International, Inc., Palo Alto, CA (US)

( * ) Notice: Subject to any disclaimer, the term of this patent is extended or adjusted under 35 U.S.C. 154(b) by 414 days.

(21) Appl. No.: 10/245,803

(22) Filed: Sep. 16, 2002

(65) Prior Publication Data

US 2003/0022348 A1    Jan. 30, 2003

Related U.S. Application Data

(60) Division of application No. 09/262,126, filed on Mar. 3, 1999, which is a continuation-in-part of application No. 09/034,630, filed on Mar. 4, 1998, now abandoned.

(51) Int. Cl.
C12N 9/44 (2006.01)
C12N 15/00 (2006.01)
C12N 1/20 (2006.01)
C12P 21/00 (2006.01)
C07H 21/04 (2006.01)

(52) U.S. Cl. .................. 435/210; 435/69.1; 435/320.1; 435/252.3; 435/252.31; 435/252.5; 536/23.2; 536/23.7

(58) Field of Classification Search .............. 435/4, 435/6, 69.1, 183, 200, 252.1, 252.3, 252.31, 435/252.5, 320.1, 210; 536/23.2, 23.4, 23.7, 536/252.31
See application file for complete search history.

(56) References Cited

U.S. PATENT DOCUMENTS

| 3,716,455 A | 2/1973 | Ueda et al. |
| 3,741,673 A | 6/1973 | Ueda et al. |
| 3,790,446 A | 2/1974 | Gunja-Smith |
| 3,827,940 A | 8/1974 | Sugimoto et al. |
| 3,897,305 A | 7/1975 | Hurst |
| 5,817,498 A | 9/1980 | McCourt et al. |
| 4,560,651 A | 12/1985 | Nielsen et al. |
| 4,628,028 A | 12/1986 | Katkocin et al. |
| 4,902,622 A | 2/1990 | Nakai et al. |

(Continued)

FOREIGN PATENT DOCUMENTS

EP    0 605 040 A    7/1994

(Continued)

OTHER PUBLICATIONS

Albertson G. D., et al, "Cloning and sequence of a type I pullulanase from an extremely themophilic anaerobic bacterium, *Caldicellulosiruptor saccharolyticus*," Biochimica et Biophysica Acta., V. 1354, N. 1, 1997, pp. 35-39.

(Continued)

*Primary Examiner*—Rebecca E. Prouty
*Assistant Examiner*—Rosanne Kosson
(74) *Attorney, Agent, or Firm*—Danisco A/S, Genencor Division

(57) ABSTRACT

The present invention relates to modified pullulanases useful in the starch industry. The present invention provides methods for producing the modified pullulanase, enzymatic compositions comprising the modified pullulanase, and methods for the saccharification of starch comprising the use of the enzymatic compositions.

30 Claims, 19 Drawing Sheets

U.S. PATENT DOCUMENTS

| | | | |
|---|---|---|---|
| 5,055,403 | A | 10/1991 | Tomimura et al. |
| 5,387,516 | A | 2/1995 | Kawai et al. |
| 5,721,127 | A | 2/1998 | Deweer et al. |
| 5,721,128 | A * | 2/1998 | Deweer et al. .............. 435/210 |
| 5,731,174 | A | 3/1998 | Deweer et al. |
| 5,736,375 | A * | 4/1998 | Deweer et al. .............. 435/210 |
| 6,074,854 | A | 6/2000 | Deweer et al. |

FOREIGN PATENT DOCUMENTS

| | | |
|---|---|---|
| GB | 1336599 | 11/1973 |

OTHER PUBLICATIONS

Ara, K. et al., "Separation of functional domains for the .Na-1,4 and .Na-1,6 hydrolytic activities of *Bacillus amylopullulanase* by limited proteolysis with papain," *Bioscience Biotechnology Biochemistry*, V. 60, N. 4, 1996 pp. 634-639.

Sauvonnet N. et al., "Extracellular secretion of pullulanase is unaffected by minor sequence changes but is usually prevented by adding reporter proteins to its N- or C-terminal end," *Journal of Bacteriology*, V. 177, N. 18, 1995, pp. 5338-5246.

Takagi, M. et al., "Diversity in size and alkaliphily of thermostable alpha-amylase-pullulanses (AapT) produced by recombinant *Escherichia coli, Bacillus subtilis* and the wild-type BVacillius sp.," *Journal of Feementation and Bioengineering*, V. 81, N. 6, 1996, pp. 557-559.

Tobimatsu t. et al: "Molecular Cloning, Sequencing and Expression of the genes encoding adenosylcobalamin-dependent diol dehydrase of *Klebsiella oxytoca*". *Journal of Biological Chemistry*, vol. 270, No. 13, pp. 7142-7148, (Mar. 1995).

Tobimatsu T. et al: "Cloning, Sequencing and high level expression of the genes encoding adenosylcobalamin-dependent glycerol dehydrase of *Klebsiella pneumoniae*", *Journal of Biological Chemistry*, vol. 271, No. 37, pp. 22352-22357, (Sep. 1996).

Tong I.T. et al.: "1,3 -propanediol production of *Eshericjia coli* expressing genes from the *Klebsiella pneumoniae* dha regulon" *Applied and Environmental Microbiology*, vol. 57, pp. 3541-3546 (1991).

Bakshi et al., "Thermostable Pullulanase from a Mesophilic *Bacillus cereus* Isolate and its Mutant UV7.4," (1992) *Biotechnology Letters*, 14:689-694.

Janse et al., "Regional sequence homologies in starch-degrading enzymes," (1993) *Curr. Genet.*, 24:400-407.

Takasaki et al., "Productions and Utilizations of β-Amylase and Pullulanase from *Bacillus cereus* var. mycoides," (1976) *Agric. Biol., Chem.*, 40:1515-1522.

Ueda et al. "Production of Isoamylase by *Sterptomyces* sp. No. 28," (1971) *J. Ferment. Tech*, 49:552-558.

Ueda et al., "Production of Isoamylase by *Escherichia intermedia*," (1967) *Applied Microbiology*, 15:492-496.

Walker, "Metabolism of the Reserve Polysaccharide of *Sterptococcus mitis*," (1968) *Biochem. J.*, 108:33-40.

Yagisawa et al., "Pullulanase of *Streptomyces* sp. No. 280," (1972) *J. Ferment. Technolo.* 50:572-558.

* cited by examiner

```
GATGGGAACACGACAACGATCATTGTCCACTATTTTGCCCTGCTGGTGATTATCAACCTTTGGAGTCTAT
                                                                              70
Asp Gly Asn Thr Thr Ile Ile Val His Tyr Phe Cys Pro Ala Gly Asp Tyr Gln Pro Trp Ser Leu

GGATGTGTGGCCAAAAGACGGAGGTGGGGCTGAATACGATTTCAATCAACCGGCTGACTCTTTTGGAGCTGT
                                                                              140
Trp Met Trp Pro Lys Asp Gly Gly Gly Ala Glu Tyr Asp Phe Asn Gln Pro Ala Asp Ser Phe Gly Ala Val

TGCAAGTGCTGATATTCCAGGAAACCCAAGTCAGGTAGGAATTATCGTTCGCACTCAAGATTGGACCAAA
                                                                              210
Ala Ser Ala Asp Ile Pro Gly Asn Pro Ser Gln Val Gly Ile Ile Val Arg Thr Gln Asp Trp Thr Lys

GATGTGAGCGCTGACCGCTACATAGATTTAAGCAAAGGAAATGAGGTGTGGCTTGTAGAAGGAAACAGCC
                                                                              280
Asp Val Ser Ala Asp Arg Tyr Ile Asp Leu Ser Lys Gly Asn Glu Val Trp Leu Val Glu Gly Asn Ser

AAATTTTTATAATGAAAAAGATGCTGAGGATGCAGCTAAACCCGCTGTAAGCAACGCTTATTTAGATGC
                                                                              350
                               98       102
Gln Ile Phe Tyr Asn Glu Lys Asp Ala Glu Asp Ala Ala Lys Pro Ala Val Ser Asn Ala Tyr Leu Asp Ala

TTCAAACCAGGTGCTGGTTAAACTTAGCCAGCCGTTAACTCTTGGGGAAGGNNNAAGCGGCTTTACGGTT
                                                                              420
Ser Asn Gln Val Leu Val Lys Leu Ser Gln Pro Leu Thr Leu Gly Glu Gly ??? Ser Gly Phe Thr Val
```

FIG._1A

```
CATGACGACACAGCAAATAAGGATATTCCAGTGACATCTGTGAAGGATGCAAGTCTTGGTCAAGATGTAA
                                                                        490
 His Asp Thr Ala Asn Lys Asp Ile Pro Val Thr Ser Val Lys Asp Ala Ser Leu Gly Gln Asp Val

CCGCTGTTTTGGCAGGTACCTTCCAACATATTTTTGGAGGTTCCGATTGGGCACCTGATAATCACAGTAC
                                                                        560
 Thr Ala Val Leu Ala Gly Thr Phe Gln His Ile Phe Gly Gly Ser Asp Trp Ala Pro Asp Asn His Ser Thr

TTTATTAAAAAAGGTGACTAACAATCTCTATCAATTCTCAGGAGATCTTCCTGAAGGAAACTACCAATAT
                                                                        630
 Leu Leu Lys Lys Val Thr Asn Asn Leu Tyr Gln Phe Ser Gly Asp Leu Pro Glu Gly Asn Tyr Gln Tyr

AAAGTGGCTTTAAATGATAGCTGGAATAATCCGAGTTACCCATCTGACAACATTAATTTAACAGTCCCTG
                                                                        700
 Lys Val Ala Leu Asn Asp Ser Trp Asn Asn Pro Ser Tyr Pro Ser Asp Asn Ile Asn Leu Thr Val Pro

CCGGCGGGTGCACACGTCACTTTTTCGTATATTCCGTCCACTCATGCAGTCTATGACACAATTAATAATCC
                                                                        770
 Ala Gly Gly Ala His Val Thr Phe Ser Tyr Ile Pro Ser Thr His Ala Val Tyr Asp Thr Ile Asn Asn Pro

TAATGCGGATTTACAAGTAGAAAGCGGGGTTAAAACGGATCTCGTGACGGTTACTCTAGGGGAAGATCCA
                                                                        840
 Asn Ala Asp Leu Gln Val Glu Ser Gly Val Lys Thr Asp Leu Val Thr Val Thr Leu Gly Glu Asp Pro
```

FIG._1B

```
GATGTGAGCCATATACTCTGTCCATTCAAACAGAGGTGATACCTCGTAATGTGC
                                                        910
Asp Val Ser His Thr Leu Ser Ile Gln Thr Asp Gly Tyr Gln Ala Lys Gln Val Ile Pro Arg Asn Val

TTAATTCATCACAGTACTACTATTCAGGAGATGATCTTGGGAATACCTATACACAGAAAGCAACAACCTT
                                                                      980
Leu Asn Ser Ser Gln│Tyr│Tyr│Tyr│Ser Gly Asp Asp Leu Gly Asn Thr Tyr Thr Gln Lys Ala Thr│Thr Phe
                309  Y              VWAP

TAAAGTCTGGGCACCAACTTCTACTCAAGTAAATGTTCTTCTTTATGACAGTGCAACGGGTTCTGTAACA
                                                                      1050
     VWAP
     Lys Val Trp Ala Pro Thr│Ser Thr Gln Val Asn Val Leu Leu Tyr Asp Ser Ala Thr Gly Ser Val Thr

AAAAATCGTACCTATGACGGCCATCGGGTGTGTGTGGGAAGCAACGGTTAATCAAAACCTTGAAAATT
                                                                    1120
Lys Ile Val Pro Met Thr Ala Ser Gly His Gly Val Trp Glu Ala Thr Val Asn Gln Asn Leu Glu Asn

GGTATTACATGTATGAGGTAACAGGCCAAGGCTCTACCCGAACGGCTGTTGATCCTTATGCAACTGCGAT
                                                                      1190
                                                 391 DPY
Trp Tyr Tyr Met Tyr Glu Val Thr Gly Gln Gly Ser Thr Arg Thr Ala Val│Asp Pro Tyr│Ala Thr Ala Ile

TGCACCAAATGGAACGAGAGGCATGATTGTGGACCTGGCTAAAACAGATCCTGCTGGCTGGAACAGTGAT
                                                                      1260
Ala Pro Asn Gly Thr Arg Gly Met Ile Val Asp Leu Ala Lys Thr Asp Pro Ala Gly Trp Asn Ser Asp
```

FIG._1C

```
AAACATATTACGCCAAAGAATATAGAAGATGAGGTCATCTATGAAATGGATGTCCGTGACTTTTCCATTG    1330
         Lys His Ile Thr Pro Lys Asn Ile Glu Asp Val |Ile Tyr Glu Met Asp Val Arg Asp Phe|Ser Ile
                            433                    A

ACCCTAATTCGGGTATGAAAAAATAAAGGGAAGTATTTGGCTCTTACAGAAAAAGGAACAAAGGGCCCTGA    1400
         Asp Pro Asn Ser Gly Met Lys Asn|Lys Gly Lys Tyr Leu Ala Leu Thr|Glu Lys Gly Thr Lys Gly Pro Asp
                                       B

CAACGTAAAGACGGGGATAGATTCCTTAAAACAACTTGGGATTACTCATGTTCAGCTTATGCCTGTTTTC    1470
         Asn Val Lys Thr Gly Ile Asp Ser Leu Lys Gln Leu|Gly Ile Thr His Val Gln Leu Met Pro Val Phe
                                                       C

GCATCTAACAGTGTCGATGAAACTGATCCAACCCAAGATAATTGGGGTTATGACCCTCGCAACTATGATG    1540
         Ala Ser Asn Ser Val Asp|Glu Thr Asp Pro Thr Gln|Asp Asn Trp Gly Tyr|Asp Pro Arg Asn Tyr Asp
                                                        YNWGY

TTCCTGAAGGGCAGTATGCTACAAATGCGAATGGTAATGCTCGTATAAAAGAGTTTAAGGAAATGGTTCT    1610
         Val Pro Glu Gly Gln Tyr Ala Thr Asn Ala Asn Gly Asn Ala Arg Ile Lys Glu Phe Lys Glu Met Val Leu

TTCACTCCATCGTGAACACATTGGGGTTAACATGGATGTGTCTATAATCATATACCTTTGCCACGCAAATC    1680
         Ser Leu His Arg Glu His Ile Gly|Val Asn Met Asp Val Val Tyr Asn His Thr Phe|Ala Thr Gln Ile
                                      547                                    I
```

FIG. 1D

```
TCTGACTTCGATAAAATTGTACCAGAATATTATTACCGTACGATGATCCAGGTAATTATACCAACGGATC
                                                                      ──── 1750
Ser Asp Phe Asp Lys│Ile Val Pro Glu Tyr Tyr Tyr Arg Thr Met│Ile Gln Val Ile Ile Pro Thr Asp
                                     D

AGGTACTGGAAATGAAATTGCANGCNGAAAGGCCAATGGTTCAAAAATTTATTGATTCCCTTAAGTA
                                                                  ──── 1820
Gln Val Leu Glu Met Lys Leu ??? Ala Glu Arg Pro Met Val Gln Lys Phe Ile Ile Asp Ser Leu Lys Tyr

TTGGGTCAATGAGTATCATATTGACGGCTTCCGTTTTGACTTAATGGGCTGCTTGGAAAAGACACGATG
                                                                    ──── 1890
Trp Val Asn│Glu Tyr His Ile Asp Gly Phe Arg Phe Asp Leu Met Ala│Leu Leu Gly Lys Asp Thr Met
               II

TCCAAAGCTGCCTCGGAGCTTCATGCTATTAATCCAGGAATTGCACTTTACGGTGAGCCATGGACGGGTG
                                                                      ──── 1960
Ser Lys Ala Ala Ser Glu Leu His Ala Ile Asn Pro Gly Ile Ala Leu│Tyr Gly Glu Pro Trp Thr│Gly
                                                                       III

GAACCTCTGCACTGCCAGATGATCAGCTTCTGACAAAAGGAGCTCAAAAGGCATGGGAGTAGCGGTGTT
                                                                    ──── 2030
Gly Thr Ser Ala Leu Pro Asp Asp Gln Leu Leu Thr Lys Gly Ala Gln Lys Gly Met Gly Val Ala Val Phe

TAATGACAATTTACGAAACGCGTTGGACGGCAATGTCTTTGATTCTTCCGCTCAAGGTTTTGCGACAGGT
                                                                     ──── 2100
Asn Asp Asn Leu Arg Asn Ala Leu Asp Gly Asn Val Phe Asp Ser Ser Ala Gln Gly Phe Ala Thr Gly
```

FIG._1E

```
GCAACAGGCTTAACTGATGCAATTAAGAAGAATGGGCGTTGAGGGGAGTATTAATGACTTTACCTCTTCACCAG  2170
 Ala Thr Gly Leu Thr Asp Ala Ile Lys Asn Gly Val Glu Gly Ser Ile Asn Asp Phe Thr Ser Ser Pro

GTGAGACAATTAACTATGTCACAAGTCATGATAACTACACCCTTTGGGACAAAATAGCCCTAAGCAATCC  2240
                                            IV
 Gly Glu Thr│Ile Asn Tyr Val Thr Ser His Asp Asn Tyr Thr Leu Trp Asp Lys│Ile Ala Leu Ser Asn Pro

TAATGATTCCGAAGGCGGATCGGATTAAAAATGGATGAACTCGCACAAGCAGTTGTTATGACCTCACAAGGC  2310
                                                                    E
 Asn Asp Ser Glu Ala Asp Arg Ile Lys Met Asp Glu Leu Ala Gln Ala Val Val│Met Thr Ser Gln Gly

GTTCCATTCATGCAAGGCGGGGAAGAAATGCTTCGTANAAAAGGCGGCAACGACAATAGTTATAATGCAG  2380
 Val Pro Phe Met Gln│Gly Gly Glu Glu Met Leu Arg ??? Lys Gly Gly Asn Asp Asn Ser Tyr Asn Ala

GCGATGCGGTCAATGAGTTTGATTGGAGCAGGAAAGCTCAATATCCAGATGTTTCAACTATTATAGCGG  2450
 Gly Asp Ala Val Asn Glu Phe Asp Trp Ser Arg Lys Ala Gln Tyr Pro Asp Val Phe Asn Tyr Tyr Ser Gly

GCTAATCCACCTTCGTCTTGATCACCCAGCCTTCCGCATGACGACAGCTAATGAAATCAATAGCCACCTC  2520
 Leu Ile His Leu Arg Leu Asp His Pro Ala Phe Arg Met Thr Thr Ala Asn Glu Ile Asn Ser His Leu
```

FIG._1F

```
CAATTCCTAAATAGTCCAGAGAACACAGTGGCCTATGAATTAACTGATCATGTTAATAAAGACAAATGGG   2590
 Gln Phe Leu Asn Ser Pro Glu Asn Thr Val Ala Tyr Glu Leu Thr Asp His Val Asn Lys Asp Lys Trp

GAAATATCATTGTTGTTTATAACCCAAATAAAACTGTAGCAACCATCAATTTGCCGAGCGGGAAATGGGC   2660
 Glu Ile Ile Val Val Tyr Asn Pro Asn Lys Thr Val Ala Thr Ile Asn Leu Pro Ser Gly Lys Trp Ala

AATCAATGCTACGAGCGGTAAGGTAGGAGAATCCACCCTTGGTCAAGCAGAGGGAAGTGTCCAAGTACCA   2730
 Ile Asn Ala Thr Ser Gly Lys Val Gly Glu Ser Thr Leu Gly Gln Ala Glu Gly Ser Val Gln Val Pro

GGTATATCTATGATGATCCTTCATCAAGAGGTAAGCCCAGACCACGGTAAAAAGTAATAGAAAA   2794
 Gly Ile Ser Met Met Ile Leu His Gln Glu Val Ser Pro Asp His Gly Lys Lys
```

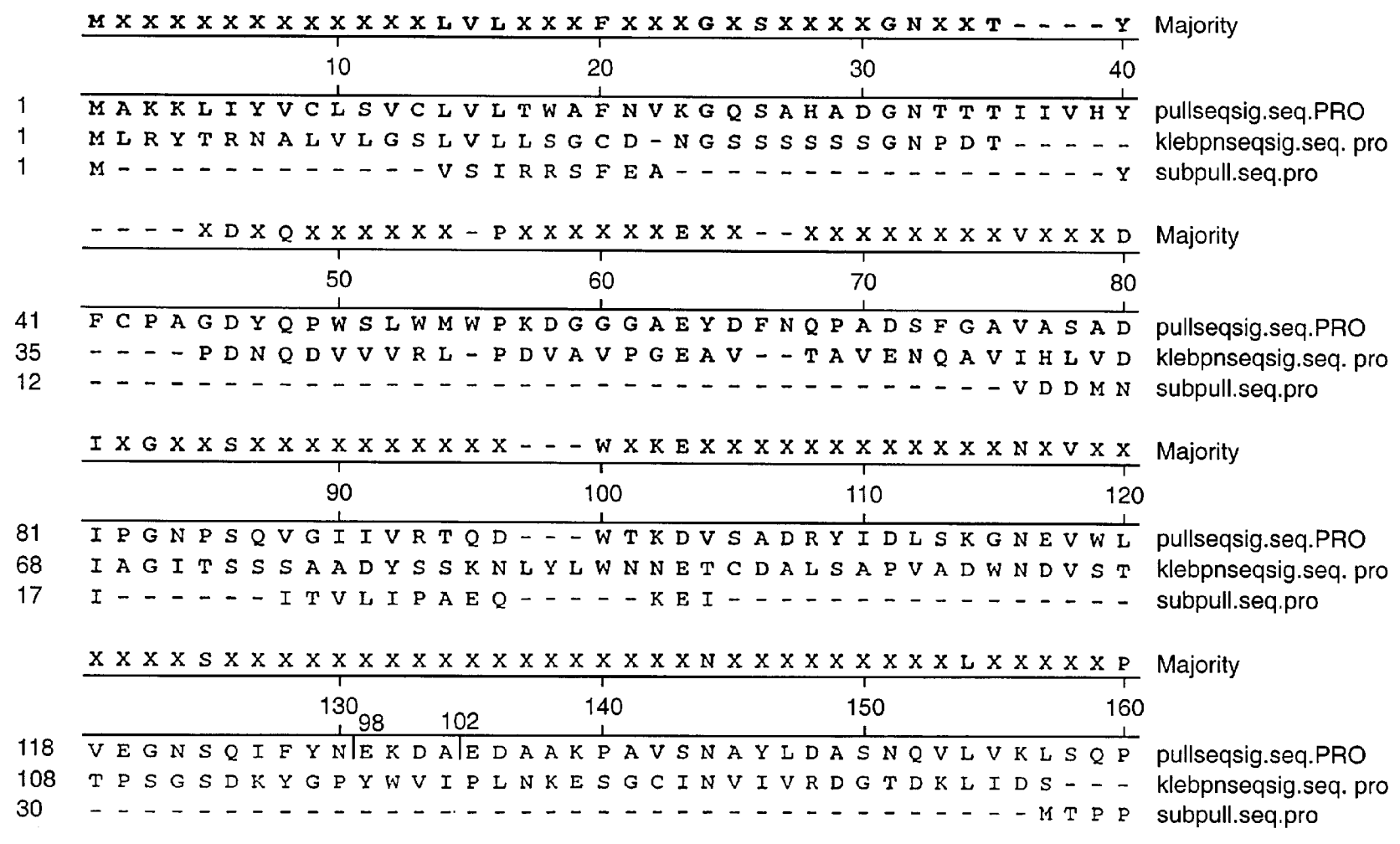

|     |                                                                  |                     |
| --- | ---------------------------------------------------------------- | ------------------- |
|     | X X L X X X X X D F T - - - - - X X X X P V X X X X X X S L X X X X X X | Majority            |
|     | 170                180                190                200    |                     |
| 158 | L T L G E G X S G F T V H D D T A N K D I P V T S V K D A S L G Q D V T A V L A | pullseqsig.seq.PRO |
| 145 | - D L R V A F G D F T - - - - - D R T V S V - I A G N S A V Y D S R A D A F R | klebpnseqsig.seq.pro |
| 34  | F R L E T E I T D F - - - - - - - - - P L A V R E E Y S L - - - - - - | subpull.seq.pro     |
|     | X X F X X X X X X X X X W X - - X X X T L L - - - - - X X X X X L Y - - - - | Majority            |
|     | 210                220                230                240    |                     |
| 198 | G T F Q H I F G G S D W A P D N H S T L L - - - - - K K V T N N L Y Q F S G D L | pullseqsig.seq.PRO |
| 177 | A A F G V A L A E A H W V - - D K N T L L W P G G Q D K P I V R L Y - - - | klebpnseqsig.seq.pro |
| 54  | - - - - - - - - - - - - - - - - - - - - - - - - - - - - - - - - - | subpull.seq.pro     |
|     | - E X X Y X Y - - X - - - - - X X X X X X X X L T V X X X X X X X V T F X X | Majority            |
|     | 250                260                270                280    |                     |
| 233 | P E G N Y Q Y K V A L N D S W N N P S Y P S D N I N L T V P A G G A H V T F S Y | pullseqsig.seq.PRO |
| 209 | - - - Y S H S S K V A A D - G E G K F T D R Y L K L T P T T V S Q Q V S M R F | klebpnseqsig.seq.pro |
| 54  | - E A K Y K Y - - - - - - - - - - - - - - - V C V S D H P V T F G K | subpull.seq.pro     |
|     | I H X X X X A X Y X X X X X X P X - X X X X V X S G X X T D L V X X A X X E D X X X X | Majority            |
|     | 290                300                310                320    |                     |
| 273 | I P S T H A V Y D T I N N P N A D L Q V E S G V K T D L V T V T L G E D P D V S | pullseqsig.seq.PRO |
| 244 | P H - - L S S Y A A A F K L P D - N A N V D E L L Q G E T V A I A A A E D G I L I | klebpnseqsig.seq.pro |
| 72  | I H C V R A - - - - - - - - - - - S S G H K T D L Q I G A V - - - | subpull.seq.pro     |

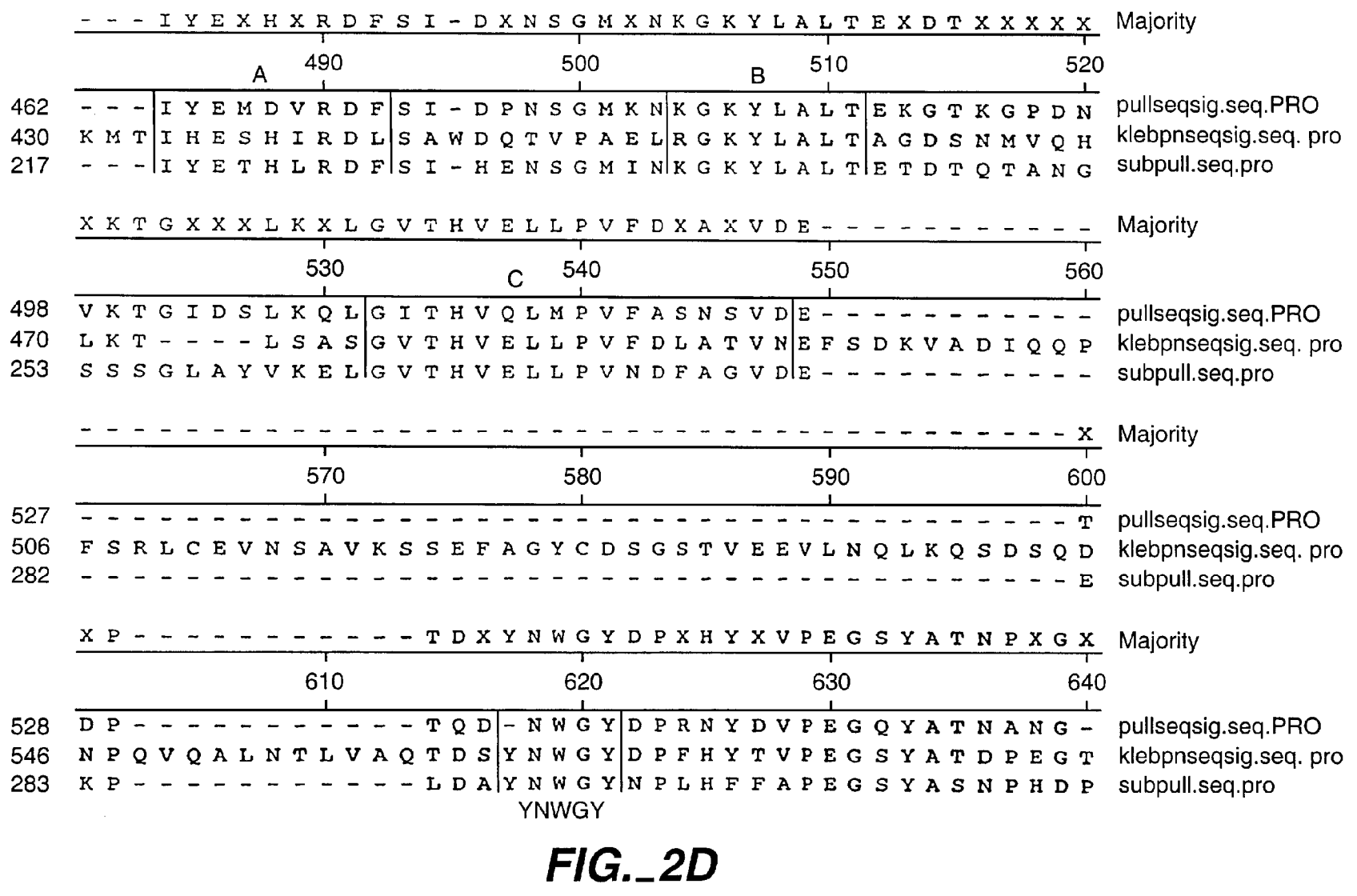

|     |  |  |  |  |  | | Source |
|---|---|---|---|---|---|---|---|
|  | X T R I K E F K X X M I X X L H Q X - G X X V I M D V V Y N H T X A X X X S D - - | | | | | 680 | Majority |
| 555 | N A R I K E F K E M V L S L H R E - H I G V N M D V V Y N H T F A T Q I S D - - | | | | | | pullseqsig.seq.PRO |
| 586 | - T R K K E F R T M I Q A I K Q D L G M N V I M D V V Y N H T N A A G P T D R T | | | | | | klebpnseqsig.seq.pro |
| 312 | Q T R K T E L K Q M I N T L H Q H - G L R V I L D V V F N H V Y K R E N S P - - | | | | | | subpull.seq.pro |
|     | - - F D K I V P X Y Y X R X X E X X X X X X X X D X A X E R R M X X K F | | | | | 720 | Majority |
| 592 | - - F D K I V P E Y Y Y Y R T M I Q V I I P T D Q V L E M K L X A E R P M V Q K F | | | | | | pullseqsig.seq.PRO |
| 625 | S V L D K I V P W Y Y Q R L N E T T G S V E S A T C C S D S A P E H R R M F A K L | | | | | | klebpnseqsig.seq.pro |
| 349 | - - F E K T V P G Y F F R H D E C G M P S N G T G V G N D I A S E R R M A R K F | | | | | | subpull.seq.pro |
|     | I A D S L X Y W X X E Y X I D G F R F D L M G X L X K D T X L X A X E X X X A X | | | | | 760 | Majority |
| 630 | I I D S L K Y W V N E Y H I D G F R F D L M A L L G K D T M S K A A S E L H A I | | | | | | pullseqsig.seq.PRO |
| 665 | I A D S L A V W T T D Y K I D G F R F D L M G Y H P K A Q I L S A W E R I K A L | | | | | | klebpnseqsig.seq.pro |
| 387 | I A D C V V Y W L E E Y N V D G F R F D L L G H L D I D T V L Y M K E K A T K A | | | | | | subpull.seq.pro |
|     | N P G I X L F G E G W D X X T S X X X X E X X X A X X K G X G I G X F N D X | | | | | 800 | Majority |
| 670 | N P G I A L Y G E P W T G G T S A L P D D Q L L T K G A Q K G M G V A V F N D N | | | | | | pullseqsig.seq.PRO |
| 705 | N P D I Y F F G E G W D S N Q S D R F E - I A S Q I N L K G T G I G T F S D R | | | | | | klebpnseqsig.seq.pro |
| 427 | K P G I L L F G E G W D L A T P L P H E Q K A A L A N A P R M P G I G F F N D M | | | | | | subpull.seq.pro |

FIG._2E

```
              LRDAVXGNX-FDSXA-----QGFAXGAGXLXXAX----    Majority
                       810           820           830           840
710   LRNALDGNV-FDSSA-----QGFATGATGLTDAI----            pullseqsig.seq.PRO
743   LRDSVRGGGPFFDSGDALRQNQGIGSGAGVLPNELASLSDD         klebpnseqsig.seq.pro
467   FRDAVKGNT-FHLKA-----TGFALGNGESAQAV----            subpull.seq.pro -----XXGXAGS-------------XXXX----A        Majority
                       850           860           870           880
738   -----KNGVEGS-------------                          pullseqsig.seq.PRO
783   QVRHLADLTRLGMAGNLADFVMIDKDGAAKKGSEIDYNGA          klebpnseqsig.seq.pro
495   -----MHGIAGS-------------SGWK----A                 subpull.seq.pro XXXXXXXPXEXINYVXSHDNXTLWDKISXXXXPQEXD-AXR         Majority
                       890    IV     900           910           920
745   INDFTSSPGETINYVTSHDNYTLWDKIALSNPNDSE-ADR          pullseqsig.seq.PRO
823   PGGYAAADPTEVVNYVSKHDNQTLWDMISYKASQEADLATR         klebpnseqsig.seq.pro
507   LAPIVPEPSQSINYVESHDNHTFWDKMSFALPQEND-SRK          subpull.seq.pro XXMQXLAXAXVMLXQGVPFXQXGXEXLRXKKGXXNSYXSG          Majority
                       930    E      940           950           960
784   IKMDELAQAVVMTSQGVPFMQGGEEMLRXKGGNDNSYNAG          pullseqsig.seq.PRO
863   VRMQAVSLATVMLGQGIAFDQQGSELLRSKSFTRDSYDSG          klebpnseqsig.seq.pro
546   RSRQRLAVAHILLAQGVPFHSGQEFFRTKQGVENSYQSS           subpull.seq.pro
```

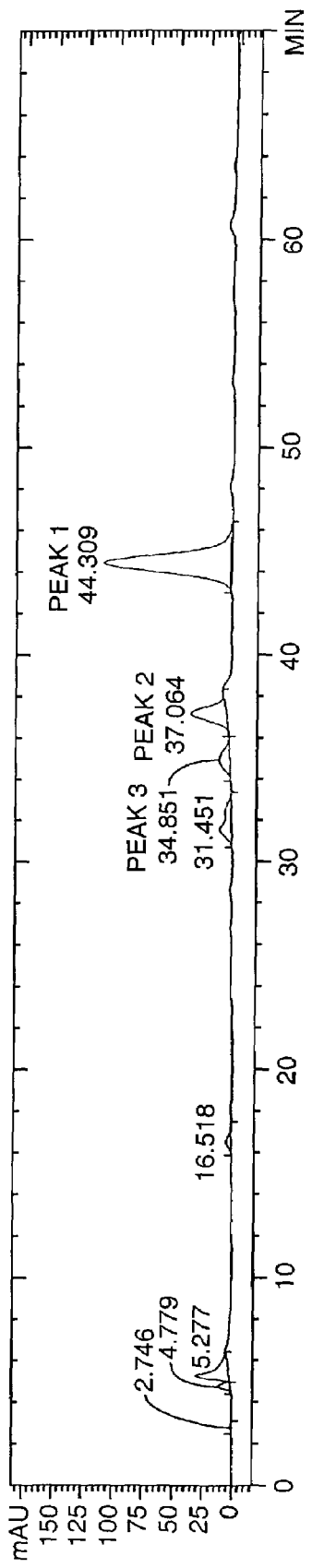
FIG._3A
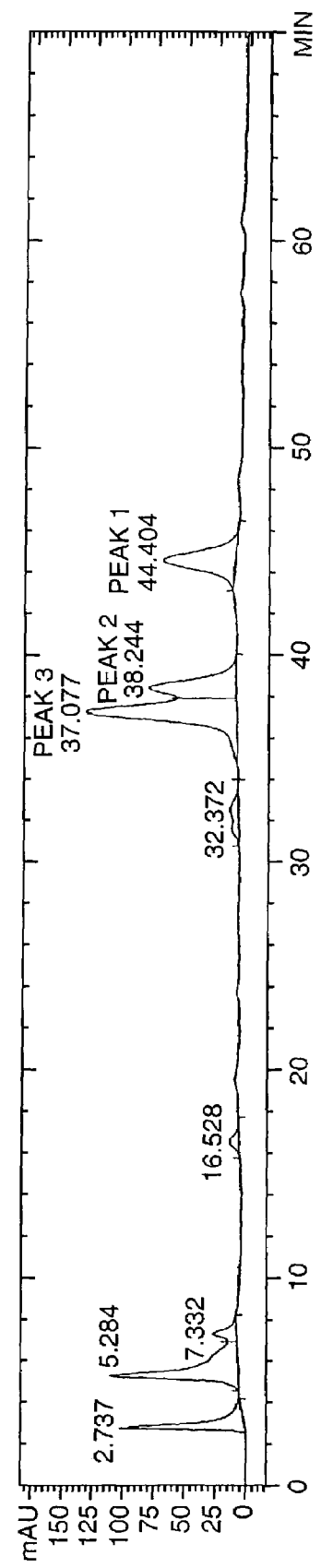
FIG._3B

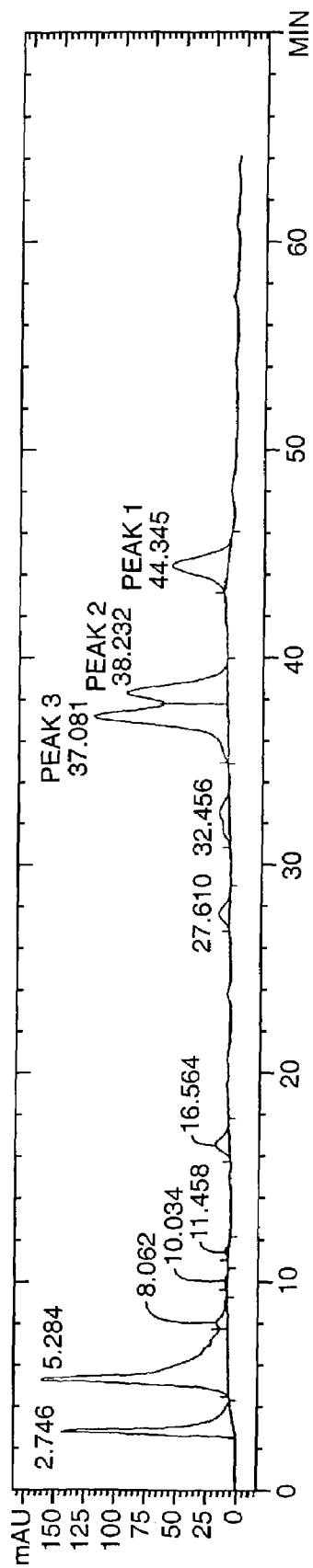
FIG._3C
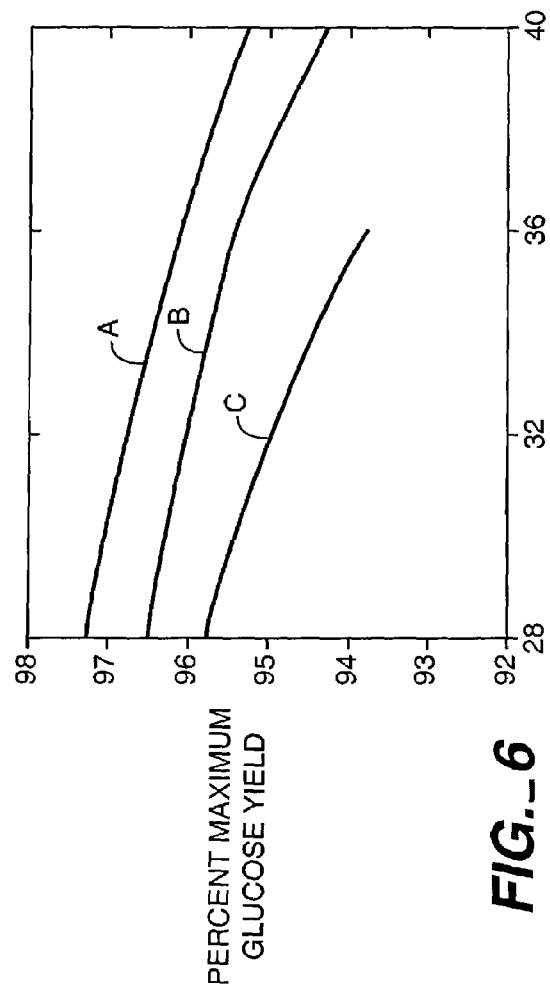
FIG._6

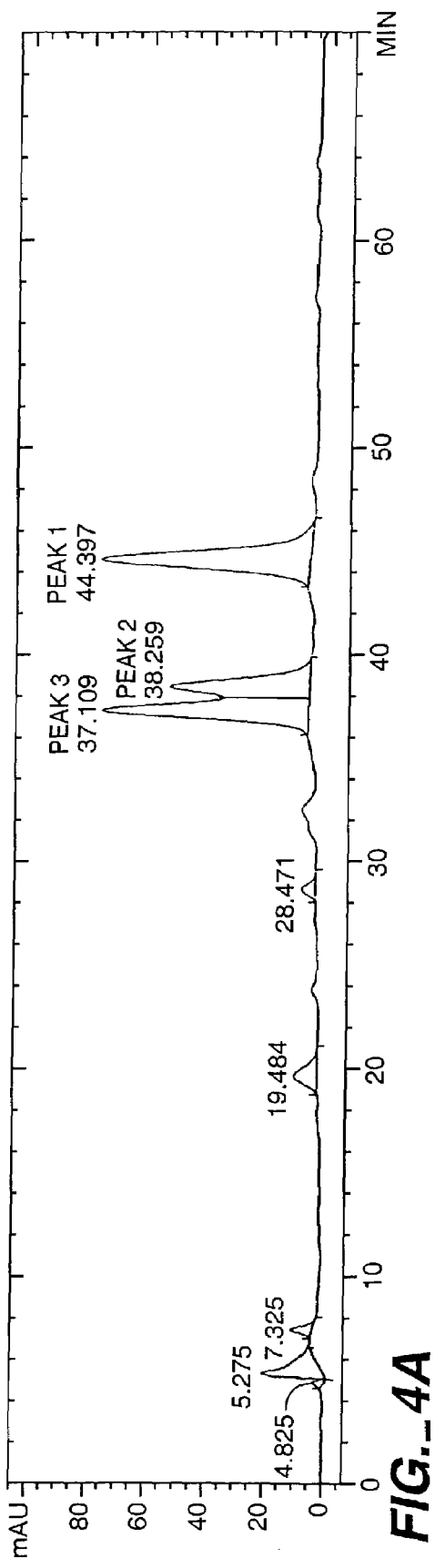
FIG._4A
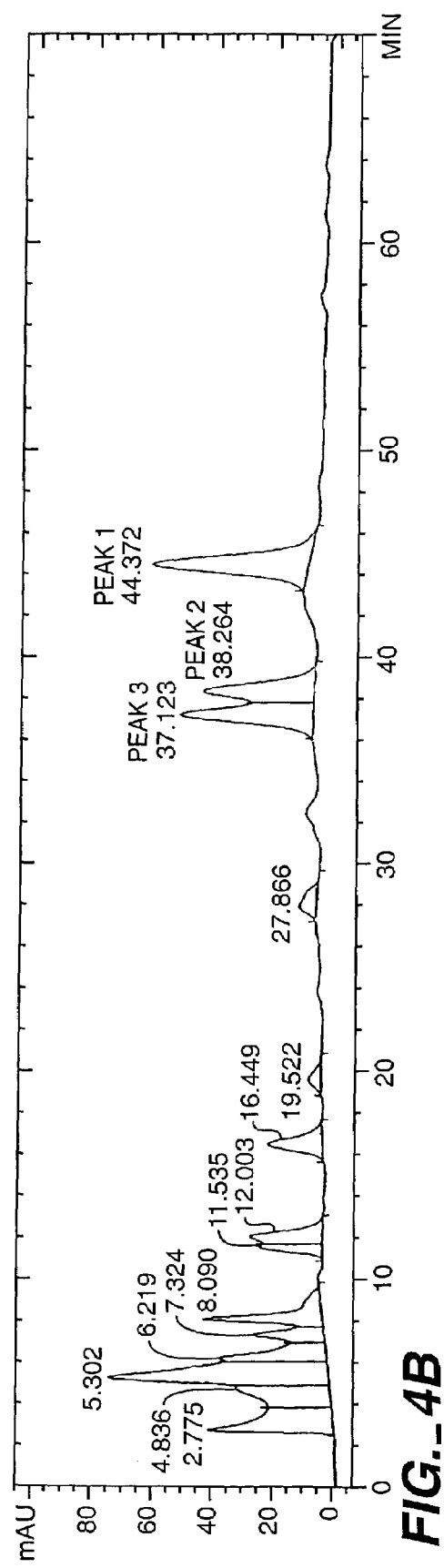
FIG._4B

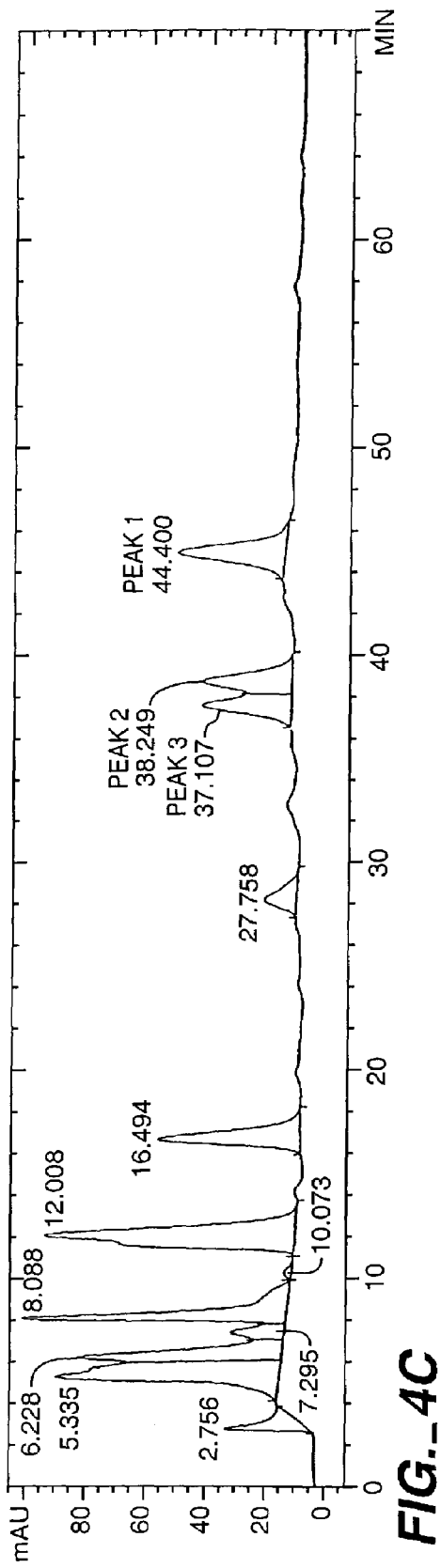
FIG._4C
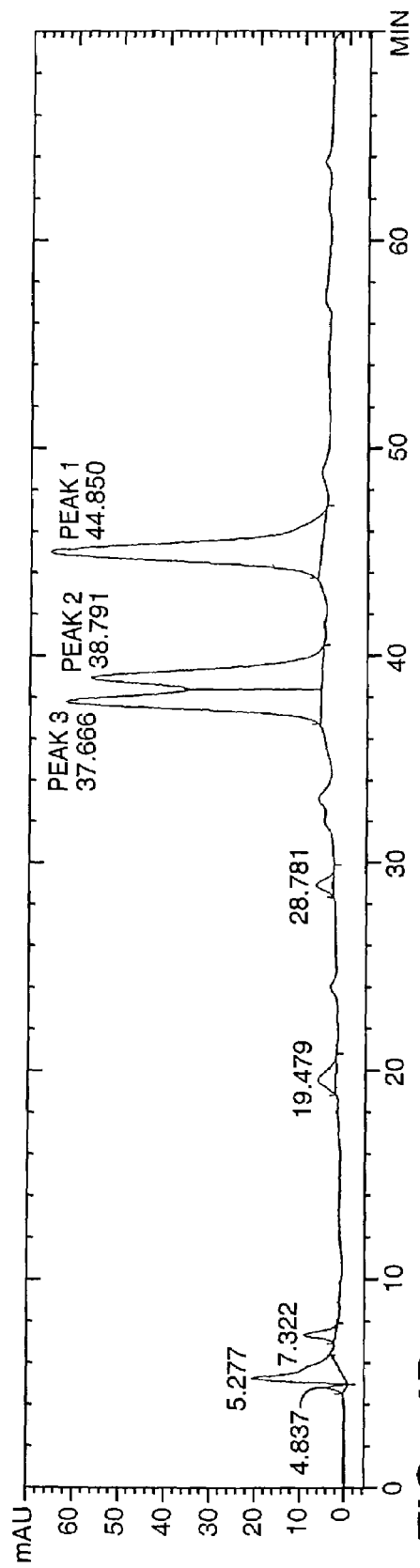
FIG._4D

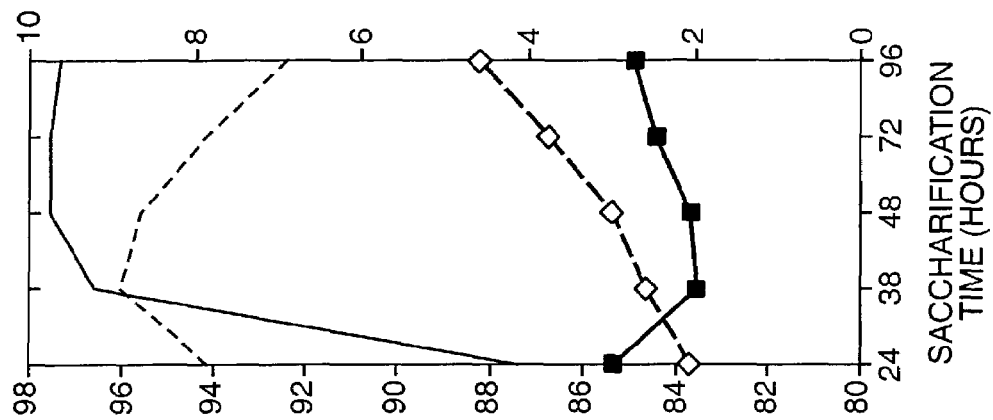
FIG._5A
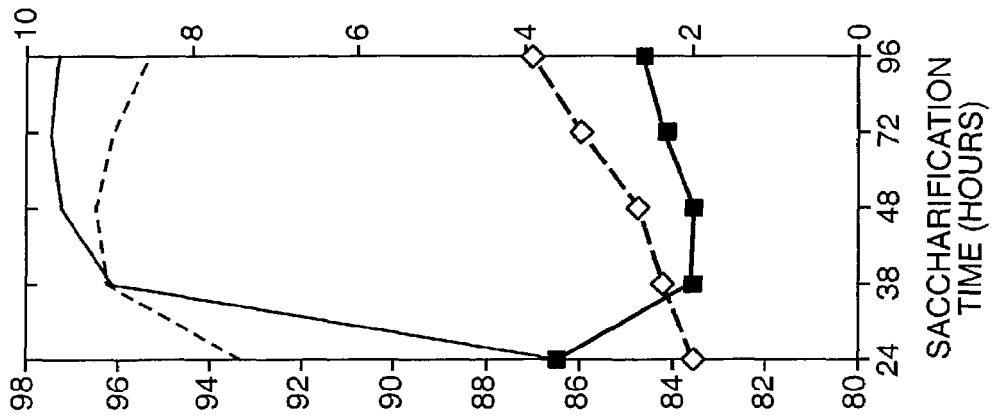
FIG._5B
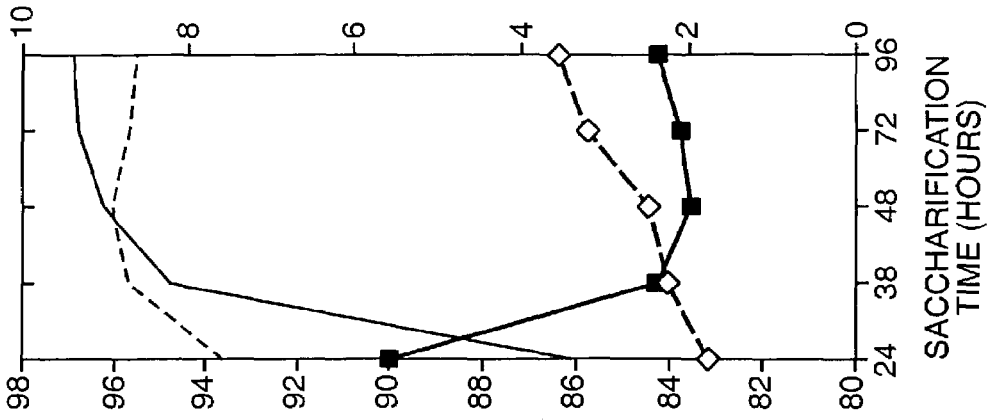
FIG._5C

MODIFIED FORMS OF PULLULANASE

RELATED APPLICATIONS

The present application is a divisional application of U.S. application Ser. No. 09/262,126, entitled "Modified Forms of Pullulanase" filed Mar. 3, 1999, which is a continuation-in-part application of U.S. application Ser. No. 09/034,630 filed Mar. 4, 1998, now abandoned, both of which are incorporated herein in there entirety.

FIELD OF THE INVENTION

The present invention relates to modified forms of pullulanase which maintain the ability to catalyze the hydrolysis of an alpha-1,6-glucosidic bond, compositions which comprise the modified pullulanase, methods of making the modified pullulanase and methods of using the modified pullulanase, especially for the saccharification of starch.

BACKGROUND OF THE INVENTION

Starch, the essential constituents of which are linear amylose and branched amylopectin glucose polymers can be converted into simple sugars by an enzymatic process carried out in two stages: one stage of liquefaction of the starch and one stage of saccharification of the liquefied starch. In order to obtain a high conversion level of the starch, pullulanase (E.C. 3.2.1.41, α-dextrin 6-glucano-hydrolase also termed alpha-1,6-glucosidase) has been used to catalyse the hydrolysis of alpha-1,6-glucosidic bonds.

Pullulanase enzymes in the art include those known to have optimum activity at acidic pH as well as those known to have activity at alkaline pH. Pullulanases described in the art include pullulanase derived from a strain of *Bacillus acidopullulyticus* described as having an optimum activity at a pH of 4-5 at 60° C. (U.S. Pat. No. 4,560,651); pullulanase derived from *Bacillus naganoensis* described as having a maximum activity at a pH of about 5, measured at 60° C. and a maximum activity at a temperature of about 62.5° C., measured at a pH of 4.5 (U.S. Pat. No. 5,055,403); pullulanase derived from *Bacillus sectorramus* described as having an optimum pH at 5.0 to 5.5 and an optimum temperature at 50° C. (U.S. Pat. No. 4,902,622); and pullulanase derived from *Bacillus brevis* PL-1 described as having activity at 4.5-5.5 at 60° C. (JP 04/023985).

Pullulanase can be used with glucoamylase or β-amylase for the production of high glucose and high maltose syrups. In addition to increasing the yields of sugars, pullulanase reduces reaction time, allows high substrate concentrations and a reduction of up to 50% in the use of glucoamylase (Bakshi et al. (1992) Biotechnology Letters vol. 14 pp. 689-694).

SUMMARY OF THE INVENTION

The present invention relates to the surprising and unexpected discovery by Applicants that modified forms of pullulanase retain the ability to catalyze the hydrolysis of an alpha-1,6-glucosidic bond. The present invention provides modified forms of pullulanase and methods for producing the modified pullulanase, especially in recombinant host microorganisms. The present invention further relates to enzymatic compositions comprising a modified form of pullulanase useful in the saccharification of starch and methods for the saccharification of starch comprising the use of the enzymatic compositions.

The present invention is based, in part, upon the discovery that when pullulanase obtained from *Bacillus deramificans* was recombinantly expressed and cultured in *Bacillus licheniformis*, the pullulanase produced was a mixture of modified forms yet the modified forms of pullulanase surprisingly retained the ability to catalyze the hydrolysis of an alpha-1,6-glucosidic bond. The modified forms comprised *B. deramificans* pullulanase truncated at the amino terminus, i.e., having a deletion of amino acids from the amino terminus, and *B. deramificans* having additional amino acids at the amino terminus of the mature pullulanase. Therefore, in one aspect, the present invention provides modified pullulanase having a deletion of amino acids from the amino terminus of a pullulanase obtainable from a gram-positive or a gram-negative microorganism as long as the modified pullulanase retains the ability to catalyze the hydrolysis of an alpha-1,6-glucosidic bond. In another aspect, the present invention provides modified pullulanase having additional amino acids at the amino terminus of a pullulanase obtainable from a gram-negative or gram positive microorganism as long as the modified pullulanase retains the ability to catalyze the hydrolysis of an alpha-1,6-glucosidic bond. The present invention also encompasses amino acid variations of a pullulanase obtainable from a gram-negative or gram positive microorganism as long as the modified pullulanase retains the ability to catalyze the hydrolysis of an alpha-1,6-glucosidic bond.

In one embodiment, the modified pullulanase is a modification of pullulanase obtainable from *Klebsiella* species. In another embodiment, the modified pullulanase is a modification of pullulanase obtainable from *Bacillus* species. In yet another embodiment, the modified pullulanase is a modification of pullulanase obtainable from *Bacillus* including but not limited to *B. subtilis, B. deramificans, B. stearothermophilus, B. naganoensis, B. flavocaldarius, B. acidopullulyticus, Bacillus* sp APC-9603, *B. sectorramus, B. cereus, B. fermus*. In a preferred embodiment, the modified pullulanase is a modification of pullulanase obtainable from *B. deramificans* having the designation T89.117D (LMG P-13056) deposited Jun. 21, 1993 under the Budapest Treaty in the LMG culture collection, University of Ghent, Laboratory of Microbiology, K. L. Ledeganckstraat 35, B-9000 GHENT, Belgium.

In one embodiment, the modified pullulanase has a deletion of about 100 amino acids from the amino terminus of a pullulanase. In another embodiment, the modified pullulanase has a deletion of about 200 amino acids from the amino terminus of a pullulanase and in yet another embodiment, the modified pullulanase has a deletion of about 300 amino acids from the amino terminus of a pullulanase.

In a further embodiment, the modified pullulanase has a deletion of 98 amino acids from the amino terminus of pullulanase obtainable from *B. deramificans*. In an additional embodiment, the modified pullulanase has a deletion of about 102 amino acids from the amino terminus of pullulanase obtainable from *B. deramificans*. In a further embodiment, the modified pullulanase has at least one additional amino acid at the amino terminus of pullulanase obtainable from *B. deramificans*. In another embodiment, the modified pullulanase has an additional amino acid residue, Alanine, added to the amino terminus of pullulanase obtainable from *B. deramificans*.

Modified forms of pullulanase having a decrease in molecular weight provide the advantage of higher specific activity (activity/unit weight) and therefore, less weight of pullulanase activity is required in a saccharification process to obtain results equivalent to the use of a naturally occurring pullulanase obtainable from or produced by a microorganism. The recombinant production of modified pullulanase as taught herein provides for enzymatic compositions comprising at least 60% and at least 80% pullulanase activity. In one embodiment, the enzymatic composition comprises at least one modified pullulanase. In another embodiment, the enzymatic composition comprises more than one modified pullulanase. Such enzymatic compositions are advantageous to the starch processing industry due to their ability to produce a high glucose yield over a shortened saccharification time without the loss of glucose yield associated with reversion reaction products. Furthermore, it was unexpectedly found that in using an enzymatic composition comprising 20% glucoamylase and 80% pullulanase, higher starting dissolved solids (DS) could be used in a saccharification process, thereby increasing production plant capacity without an increase in capital investment. Additionally, saccharification at higher dissolved solids increases mechanical compression capacity thereby providing for a more energy efficient process.

In one embodiment, the present invention provides modified pullulanase produced by the method comprising the steps of obtaining a recombinant host cell comprising nucleic acid encoding mature pullulanase, culturing said host cell under conditions suitable for the production of modified pullulanase and optionally recovering the modified pullulanase. In one embodiment, the host cell is Bacillus, including but not limited to B. subtilis, B. licheniformis, B. lentus, B. brevis, B. stearothermophilus, B. alkalophilus, B. amyloliquefaciens, B. coagulans, B. circulans, B. lautus and Bacillus thuringiensis. In a preferred embodiment, the Bacillus cell is B. licheniformis which comprises a first gene encoding the Carlsberg protease and a second gene encoding endo Glu C, the first and/or second gene which codes for the protease(s) having been altered in the Bacillus species such that the protease activity is essentially eliminated and the nucleic acid encoding the mature pullulanase is obtainable from B. deramificans.

In an alternative embodiment, the present invention provides methods for the production of a modified pullulanase in a recombinant host cell comprising the steps of obtaining a recombinant microorganism comprising nucleic acid encoding a modified pullulanase, culturing the microorganism under conditions suitable for the production of the modified pullulanase and optionally recovering the modified pullulanase produced. In one embodiment, the host cell is a gram-negative or gram-positive microorganism. In another embodiment, the host cell is a Bacillus including but not limited to B. subtilis, B. licheniformis, B. lentus, B. brevis, B. stearothermophilus, B. alkalophilus, B. amyloliquefaciens, B. coagulans, B. circulans, B. lautus and Bacillus thuringiensis. In another embodiment, the Bacillus cell is B. licheniformis which comprises a first gene encoding the Carlsberg protease and a second gene encoding endo Glu C, the first and/or second gene which codes for the protease(s) having been altered in the Bacillus species such that the protease activity is essentially eliminated and the nucleic acid encodes a modified pullulanase that is a modification of pullulanase obtainable from B. deramificans.

The present invention also provides nucleic acid comprising a polynucleotide sequence encoding modified pullulanase. In one embodiment, the nucleic acid has at least 70% identity, at least 80% identity, at least 90% identity or at least 95% identity to the polynucleotide sequence shown in SEQ ID NO: 1, which encodes pullulanase obtainable from B. deramificans. The present invention also provides expression vectors and host microorganisms comprising nucleic acid encoding a modified pullulanase of the present invention.

The present invention provides an enzymatic composition comprising at least one modified pullulanase of the present invention. In one embodiment, the enzymatic composition comprises multiple modified pullulanase forms. In another embodiment, the composition further comprises an enzyme selected from the group consisting of glucoamylase, alpha-amylase, beta-amylase, alpha-glucosidase, isoamylase, cyclomaltodextrin, glucotransferase, beta-glucanase, glucose isomerase, saccharifying enzymes, and/or enzymes which cleave glucosidic bonds. In a preferred embodiment, the enzymatic composition comprises a modified pullulanase and glucoamylase. In one embodiment, the glucoamylase is derived from an Aspergillus strain. In another embodiment, the glucoamylase is derived from an Aspergillus strain including but not limited to Aspergillus niger, Aspergillus awamori and Aspergillus foetidus. The enzymatic composition may be in a solid form or a liquid form. In one embodiment of the present invention, the enzymatic composition comprises at least 60% modified pullulanase and in another embodiment, the composition comprises at least 80% modified pullulanase.

The present invention also provides a process for the saccharification of starch, wherein said process allows for reduced concentrations of saccharification reversion by-products, comprising the step of contacting aqueous liquified starch with an enzyme composition comprising modified pullulanase. In one embodiment, the process further comprises the steps of heating said liquified starch, and recovering product. In one embodiment of the process, the enzyme composition further comprises glucoamylase. In another embodiment of the process, the contacting is at a pH of about less than or equal to 7.0 and greater than or equal to 3 and in yet another, the pH is about 4.2. In a further embodiment of the process said heating is at a temperature range of between 55 and 65 degrees C. In another embodiment, the temperature is about 60 degrees C.

BRIEF DESCRIPTION OF THE DRAWINGS

FIGS. 1A-1G illustrate the nucleic acid (SEQ ID NO:1) encoding the mature amino acid (SEQ ID NO:2) sequence of pullulanase obtainable from B. deramificans.

FIGS. 2A-2G are an alignment of amino acid sequences of pullulanase obtainable from B. deramificans (designated pullseqsig.seq.PRO) (SEQ ID NO:2), B. subtilis (designated subpull.seq.pro) (SEQ ID NO:3), and K. pneumonia (designated klebpnseqsig.seq.pro) (SEQ ID NO:4) showing the conserved domains and variability of the amino terminus of these pullulanases. This alignment also includes the signal sequences for the respective pullulanases.

FIGS. 3A-3C illustrate a timecourse of fermentation and the various species of modified pullulanase that are formed during the fermentation. Peak 1 designates the mature B. deramificans pullulanase having a molecular weight of 105 kD; peak 2 designates the modified pullulanase which has a deletion of 102 amino acids from the amino terminus of mature B. deramificans pullulanase; and peak 3 designates the modified pullulanase which has a deletion of 98 amino acids from the amino terminus as measured by standard HPLC analysis. FIG. 3A illustrates the fermentation over 37 hours. FIG. 3B illustrates the fermentation over 60 hours. FIG. 3C illustrates the fermentation over 70 hours.

FIGS. 4A-4D illustrate the stability of the modified pullulanase species as a function of pH as measured by standard HPLC analysis. FIG. 4A illustrates the pullulanase stability at 24 hours at a pH of 4.5 at room temperature. FIG. 4B illustrates the pullulanase stability at 24 hours at a pH of 5.5 at room temperature. FIG. 4C illustrates the pullulanase stability at 24 hours at a pH of 6.5 at room temperature. FIG. 4D illustrates the pullulanase stability at 96 hours at a pH of 4.5 at room temperature.

FIGS. 5A-5C illustrate the effect of enzymatic compositions comprising various pullulanase and glucoamylase concentrations on the final glucose yield and disaccharide formation over saccharification time. The solid line refers to an enzymatic blend comprising 80% pullulanase activity (including modified pullulanase having a deletion of 98 amino acids from the amino terminus of *B. deramificans*; modified pullulanase having a deletion of 102 amino acids from the amino terminus of *B. deramificans*; mature *B. deramificans* pullulanase and mature *B. deramificans* pullulanase having an additional amino acid (alanine) on the amino terminus) and 20% glucoamylase (20:80). The dotted line refers to an enzymatic composition comprising an enzyme blend comprising 75% glucoamylase obtainable from Aspergillus sp. and 25% mature pullulanase obtainable from *B. deramificans* (75:25). The solid line with squares refers to di-saccharides formed with the enzyme blend comprising 20% glucoamylase and 80% pullulanase activity as described above (20:80) over the saccharification time and the dotted line with circles refers to the di-saccharides formed with the 75:25 over the saccharification time. The left X-axis is % glucose yield and the right X-axis is % di-saccharides. FIG. 5A refers to the saccharification process using 0.550 liters of enzymatic composition per metric ton of dissolved solids; FIG. 5B refers to the saccharification process using 0.635 liters of enzymatic composition per metric ton of dissolved solids; FIG. 5C refers to the saccharification process using 0.718 liters of enzymatic composition per metric ton of dissolved solids. This Figure illustrates that a 20:80 enzymatic composition is able to increase the final glucose yield without an increase in undesirable disaccharide formation.

FIG. 6 illustrates the effect of dissolved solids (%w/w) (Y axis) on the final glucose yield during saccharification of liquefied starch using enzyme compositions 20:80, 75:25, and 100% glucoamylase at 0.55 liters of enzyme per metric ton of dissolved solids. Line A is the enzymatic composition 20:80 described in FIGS. 5A-5C; line B is the enzymatic composition 75:25 and line C is an enzymatic composition comprising 100% glucoamylase.

DETAILED DESCRIPTION

Definitions

The term pullulanase as used herein refers to any enzyme having the ability to cleave the alpha-1,6 glucoside bond in starch to produce straight chain amyloses. These enzymes are preferably classified in EC 3.2.1.41 and include neopullulanases.

As shown in FIGS. 2A-2D, there are regions of similarity among pullulanases obtainable from gram positive and gram negative microorganisms. The amino acid alignment of pullulanase obtainable from *Bacillus deramificans* with pullulanase obtainable from *K. pneumonia* and *B. subtilis* reveals that when the conserved domains are aligned, the amino terminus not associated with the conserved domains is of varying length. As used herein, the term "modified" when referring to pullulanase means a pullulanase enzyme in which the conserved domains are retained while any length of amino acids in the amino terminus portion of the naturally occurring amino acid sequence not associated with the conserved domains has been altered by a deletion of these amino acid residues or by addition of at least one amino acid to the amino terminus as long as the modified pullulanase retains the ability to catalyze the hydrolysis of an alpha-1,6-glucosidic bond. The deletion in the amino terminal amino acids of a pullulanase can be of varying length, but is at least three amino acids in length and the deletion can go no further than the beginning of the first conserved domain which in *B. deramificans* is the tyrosine at amino acid residue 310 as shown in FIGS. 1A-1E. In one embodiment, the deletion is about 100 amino acids from the amino terminus of the mature pullulanase. In another embodiment, the deletion is about 200 amino acids from the amino terminus of the mature pullulanase and in another embodiment, the deletion is about 300 amino acids from the amino terminus of the mature pullulanase. In a preferred embodiment, the modification is a deletion of 98 amino acids from the amino terminus of *B. deramificans*. In yet another embodiment, the deletion is 102 amino acids from the amino terminus of *B. deramificans*. In a further embodiment, the modification is an addition of at least one amino acid to the amino terminus of the naturally occurring mature pullulanase obtainable from *Bacillus deramificans*. In another preferred embodiment, the amino acid residue, Alanine, is added to the amino terminus of the mature pullulanase. As used herein the term "mature" refers to a protein which includes the N-terminal amino acid residue found after the natural cleavage site of the signal sequence.

Figure 2C:
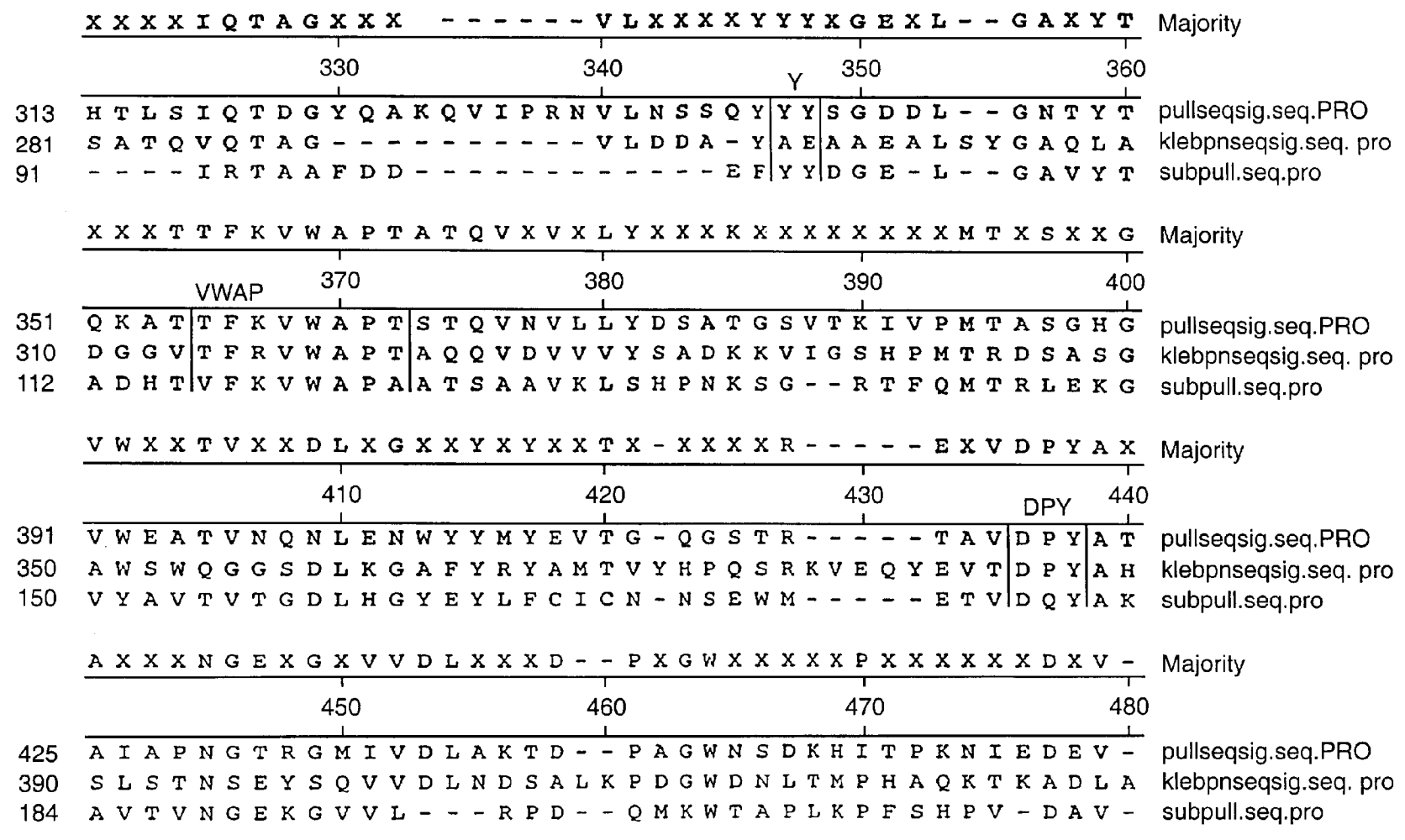
Figure 2G:
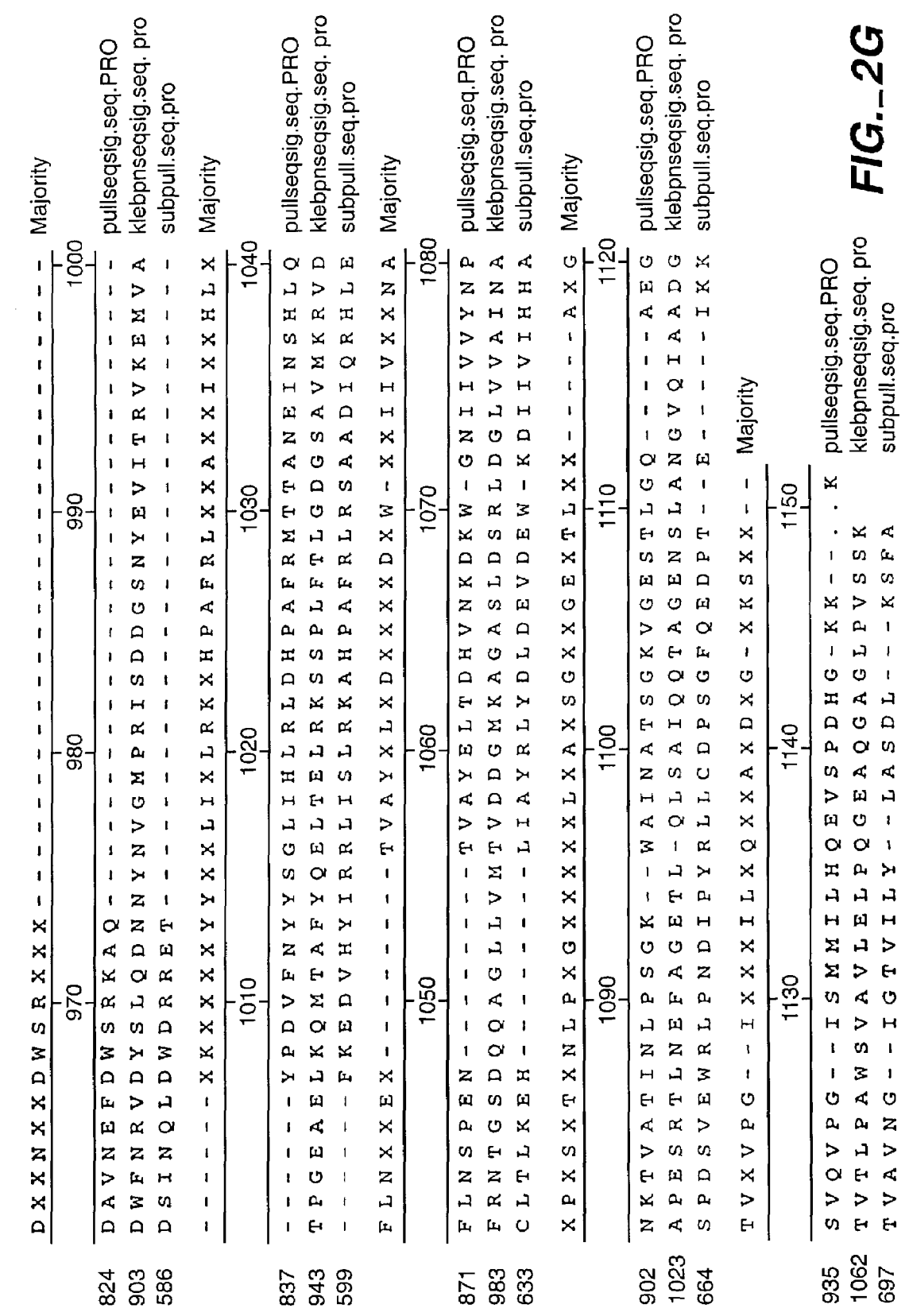

As illustrated in FIGS. 2A-2D, *B. deramificans* pullulanase and *K. pneumonia* pullulanase are examples of pullulanases having similarities in the length of the amino terminus up to the beginning of the first conserved domain (which in *B. deramificans* is amino acid residue 310 Tyrosine). *B. subtilis* pullulanase is an example of a pullulanase having a shorter length of amino acid residues up to the beginning of the first conserved domain as shown in FIG. 2B.

As used herein, "nucleic acid" refers to a nucleotide or polynucleotide sequence, and fragments or portions thereof, and to DNA or RNA of genomic or synthetic origin which may be double-stranded or single-stranded, whether representing the sense or antisense strand. As used herein "amino acid" refers to peptide or protein sequences or portions thereof. The present invention encompasses polynucleotides having at least 70%, at least 80%, at least 90% and at least 95% identity to the polynucleotide encoding *B. deramificans* pullulanase, as well as polynucleotides encoding a pullulanase activity capable of hybridizing to nucleic acid encoding *B. deramificans* pullulanase under conditions of high stringency.

The terms "isolated" or "purified" as used herein refer to a nucleic acid or amino acid that is removed from at least one component with which it is naturally associated.

DETAILED DESCRIPTION OF THE PREFERRED EMBODIMENTS

The present invention relates to the discovery that pullulanase recombinantly produced in a *Bacillus* host is modified yet unexpectedly retains the ability to catalyze the hydrolysis of an alpha-1,6-glucosidic bond. The modification of the pullulanase product recombinantly produced appears to be a result of misprocessing of the signal sequence by a signal peptidase as well as susceptibility to extracellular proteolytic processing. The modified pullulanase is used to produce compositions and methods useful in the starch industry.

I. Pullulanase Sequences

The present invention encompasses any modified pullulanase which retains the ability to catalyze the hydrolysis of an alpha-1,6-glucosidic bond. A variety of pullulanases have been described in the art, including those obtainable from or naturally produced by gram-positive microorganisms as well as gram-negative microorganisms. Microorganisms that naturally produce pullulanase include, but are not limited to, *B. deramificans* (having the designation T89.117D in the LMG culture collection, University of Ghent, Laboratory of Microbiology-K. L. Ledeganckstraat 35, B-9000 Ghent, Belgium) the nucleic acid (SEQ ID NO:1) and amino acid (SEQ ID NO:2) sequence being disclosed in FIGS. 1A-1E; *B. naganoensis* (American Type Culture Collection, ATCC accession number 53909), disclosed in U.S. Pat. No. 5,056,403 issued Oct. 8, 1991; *B. acidopullulyticus* (National Collection of Industrial Bacteria, Torry Research Station, Aberdeen, Scotland, NCIB 11607, NCIB 11610, NCIB 11611, NCIB 11636, NCIB 11637, NCIB 11639, NCIB 11638, NCIB 11647, NCIB 11777), disclosed in U.S. Pat. No. 4,560,651, issued Dec. 24, 1985; *B. sectorramus* (Fermentation Research Institute, Agency of Industrial Science and Technology, 1-3, Higashi 1-chome, Yatabe-machi, Tsukuba-gun, Ibaraki 305 Japan FERM BP-1471), disclosed in U.S. Pat. No. 4,902,622, issued Feb. 20, 1998; *Bacillus* FERM BP-4204 disclosed in U.S. Pat. No. 5,387,516 issued Feb. 7, 1995; *B. stearothermophilus* (SWISS-PROT id NEPU_BACST ac P38940); *B. cereus* var. *mycoides* (IFO 300) described in Y. Takasaki et al., 1976, Agric. Biol. Chem. 40:1515; *B. fermus* (IFO 3330); *Klebsiella pneumonia*, U.S. Pat. No. 3,897,305 (SWISS-PROT id PULA_KLEPN ac P07206 and ATCC 15050; *Klebsiella aerogenes* (SWISS-PROT id PULA_KLEAE ac P07811); *Thermoanaerobium brockii* (ATCC No. 33075), U.S. Pat. No. 4,628,028; *Streptomyces* sp. described in M. Yagisawa et al., 1972, J. Ferment. Technolo. 50:572; *Caldicellulosiruptor saccharolyticus* disclosed in Albertson et al., 1997, Biochimica et Biophysica Acta 1354:35-39; *Eschericia intermedia* Ueda et al., 1967, Applied Microbiology vol 15:492 U.S. Pat. No. 3,716,455 (issued 1973) *Streptococcus mites* Walker 1968, Biochem. J., vol. 108:33; *Streptomyces* (Ueda et al., 1971, J. Ferment. Tech. Vol. 49: 552); *Flavochromogenes*, as described in U.S. Pat. No. 4,902,622; *Flavobacterium esteromaticum* Japanese Patent Application Kokoku 18826/1973; *Cytophaga* U.S. Pat. No. 3,790,446 issued 1974; *Lactobacillus, Micrococcus, Nocardia, Staphylococcus, Azotobactger*, Sarcina England patent 11260418, U.S. Pat. No. 3,827940 issued 1974; and Actinomycetes U.S. Pat. No. 3,741,873 issued 1973. Any pullulanase known in the art which comprises the conserved pullulanase regions as shown in FIGS. 2A-2D can be modified to have deletions or additions to the amino terminus as long as the modified pullulanase retains the ability to catalyse the hydrolysis of an alpha-1,6-glucosidic bond.

A nucleic acid sequence encoding a pullulanase can be obtained from a microorganism through hybridization technology using the nucleic acid sequences that encode the conserved domains of pullulanases (as shown in FIGS. 2A-2D) as primers and/or probes. (U.S. Pat. No. 5,514,576; Southern, E. 1979, Methods Enzymol. 68:152-176; Saiki, et al. 1988, Science 239:487-491). In one embodiment disclosed herein for *B. deramificans* pullulanase, the naturally occurring nucleic acid (SEQ ID NO:1) encoding a mature pullulanase was introduced into *B. licheniformis* having a deletion of the Carlsburg protease (Jacobs et al., 1985, Nucleic Acid Research 13:8913-8926) and endoGluC proteases (Kakudo et al., 1992, Journal of Bio. Chem. Vol. 267:23782-23788), the *B. licheniformis* comprising the nucleic acid encoding the mature pullulanase was cultured under conditions suitable for expression of said nucleic acid and secretion of the expressed pullulanase. The protease deletions in *B. licheniformis* were made through techniques known to those of skill in the art.

Through the fermentation process, the expressed pullulanase was cleaved extracellularly into multiple pullulanase species which retain the ability to catalyse the hydrolysis of alpha-1,6-glucosidic bonds. The multiple species are a pullulanase having a deletion of the first 98 amino acid residues from the amino terminus and starting at glutamic acid, a pullulanase having a deletion of the first 102 amino acid residues from the amino terminus (and starting at glutamic acid), and a pullulanase having the addition of at least one amino acid residue to the amino terminus of the mature pullulanase, along with the mature pullulanase as shown in FIGS. 1A-1E. As shown in Example II, it appears that the extracellular cleaving into multiple species may be due to a protease activity in the fermentation broth.

In an alternate embodiment of the present invention, nucleic acid encoding a mature pullulanase is genetically engineered to create a modified pullulanase having a deletion of amino acids at the amino terminus or having amino acids added at the amino terminus. The genetically engineered pullulanase is introduced into a host cell, preferably a *Bacillus* host cell, and cultured under conditions suitable for expression and secretion of the modified pullulanase. Nucleic acid encoding a mature pullulanase can be a naturally occurring sequence, a variant form of the nucleic acid or from any source, whether natural, synthetic, or recombinant.

Regional sequence homologies in starch degrading enzymes have been disclosed in Janse et al. (1993) Curr. Genet. 24:400-407. Janse disclose the conserved regions in α-amylases that are implicated in substrate binding, catalysis, and calcium binding. An amino acid alignment of *B. deramificans, B. subtilis* and *K. pneumonia* pullulanases is shown in FIGS. 2A-2D.

When homologies were compared in starch degrading enzymes by Janse et al., four conserved regions where noted, Regions 1, 2, 3, and 4. Three of these regions were associated with specific functions found in starch-degrading enzymes: region 1: DWINH; region 2: GFRLDMKH; and region 4: FVDVHD. Further analysis of five Type I pullulanase sequences by Albertson et al.(1997, Biochimica et Biophysica Acta 1354:35-39) revealed other conserved regions among a group of gram-positive and gram-negative pullulanases. These include regions called DPY, A, B, C, D, E, and YNWGY. Two regions, DPY and YNWGY were identified as being characteristic of true pullulanases. Conserved regions A-E align closely with β-sheet elements as defined for amylases. In addition, two other conserved regions closer to the N-terminus of the pullulanase, referred to as Y and VWAP in FIGS. 2A-2D, indicate the limits of amino acid truncations in the N-terminal of pullulanases in general. This prediction is based on the lack of further conserved regions of identity among the known pullulanases beyond the Y region as one proceeds to the N-terminus. Due to the size heterogeneity of the known pullulanases, the N-terminal regions beyond the Y region call vary between approximately 100-300 amino acids. For the *B. deramificans* pullulanase, a truncation of 309 residues would leave the first conserved region (Y at amino acid residue 310 in FIGS. 1A-1E) intact.

*B. deramificans* Pullulanase

Mature *B. deramificans* pullulanase comprises the amino acid sequence (SEQ ID NO: 2) shown in FIGS. 1A-1E. The following description of characteristics refers to mature *B. deramificans* pullulanase. *B. deramificans* pullulanase has an isoelectric point of between 4.1 and 4.5, is heat stable and active in a wide temperature range. The *B. deramificans* pullulanase is active at an acid pH. This pullulanase is capable of catalyzing the hydrolysis of α-1,6-glucosidic bonds present both in amylopectin and in pullulan. It breaks down pullulan into maltotriose and amylopectin into amylose. The polysaccharide pullulan, which is a polymer of maltotriose units connected to each other by alpha-1,6-linkages can be obtained from Aureobasidium pullulans (Pullaria pullulans) by the procedure of Ueda et al., Applied Microbiology, 11, 211-215 1963).

*B. deramificans* pullulanase hydrolyses amylopectin to form oligosaccharides (maltooligosaccharides). During this hydrolysis, the formation of oligosaccharides made up of about 13 glucose units (degree of polymerization of 13, this molecule is also called "chain A") is observed, followed by the formation of oligosaccharides made up of about 47 glucose units (degree of polymerization of 47, this molecule is also called "chain B').

The oligosaccharides with chains A and B are defined with reference to D. J. MANNERS ("Structural Analysis of Starch components by Debranching Enzymes" in "New Approaches to research on Cereal Carbohydrates", Amsterdam, 1985, pages 45-54) and B. E. ENEVOLDSEN ("Aspects of the fine structure of starch" in "New Approaches to research on Cereal Carbohydrates", Amsterdam, 1985, pages 55-60).

The *B. deramificans* pullulanase hydrolyses potato amylopectin. This hydrolysis can be carried out with an aqueous suspension of amylopectin in the presence of the pullulanase under the conditions of optimum activity of the pullulanase, that is to say at a temperature of about 60° C. and at a pH of about 4.3.

The *B. deramificans* pullulanase catalyses the condensation reaction of maltose to form tetraholosides (oligosaccharides having 4 glucose units).

The *B. deramificans* pullulanase has a half-life of about 55 hours, measured at a temperature of about 60° C. in a solution buffered at a pH of about 4.5 and in the absence of substrate.

Half-life means that the pullulanase shows a relative enzymatic activity of at least 50%, measured after an incubation of 55 hours at a temperature of about 60° C. in a solution buffered at a pH of about 4.5 and in the absence of substrate.

The *B. deramificans* pullulanase is heat stable at an acid pH and shows a relative enzymatic activity of at least 55%, measured after an incubation of 40 hours at a temperature of 60° C. in a solution buffered at a pH of about 4.5 and in the absence of substrate. It shows a relative enzymatic activity of at least 70%, measured after an incubation of 24 hours under these same conditions.

Relative enzymatic activity means the ratio between the enzymatic activity measured in the course of a test carried out under the given pH, temperature, substrate and duration conditions, and the maximum enzymatic activity measured in the course of this same test, the enzymatic activity being measured starting from the hydrolysis of pullulane and the maximum enzymatic activity being fixed arbitrarily at the value of 100.

The *B. deramificans* pullulanase is furthermore stable in a wide range of acid pH values. Under the conditions described below, it is active at a pH greater than or equal to 3. In fact, the *B. deramificans* pullulanase shows a relative enzymatic activity of at least 85%, measured after an incubation of 60 minutes at a temperature of about 60° C. in the absence of substrate and in a pH range greater than or equal to about 3.5.

Under the conditions described below, it is active at a pH of less than or equal to 7. In fact, the *B. deramificans* pullulanase shows a relative enzymatic activity of at least 85%, measured after an incubation of 60 minutes at a temperature of about 60° C. in the absence of substrate and in a pH range less than or equal to about 5.8.

It preferably shows a relative enzymatic activity of greater than 90%, measured in a pH range of between about 3.8 and about 5 under these same conditions.

The *B. deramificans* pullulanase develops an optimum enzymatic activity, measured at a temperature of about 60° C., in a pH range greater than 4.0. It develops an optimum enzymatic activity, measured at a temperature of about 60° C., in a pH range less than 4.8. The *B. deramificans* pullulanase preferably develops an optimum enzymatic activity, measured at a temperature of about 60° C., at a pH of about 4.3. Furthermore, it develops an optimum enzymatic activity, measured at a pH of about 4.3, in a temperature range of between 55 and 65° C., and more particularly at 60° C.

The *B. deramificans* pullulanase develops an enzymatic activity of more than 80% of the maximum enzymatic activity (the maximum enzymatic activity being measured at a temperature of 60° C. and at a pH of 4.3) in a pH range between about 3.8 and about 4.9 at a temperature of about 60° C.

The strain *Bacillus deramificans* T 89.117D has been deposited in the collection called BELGIAN CORRDINATED COLLECTIONS OF MICROORGANISM (LMG culture collection, University of Ghent, Laboratory of Microbiology—K. L. Ledeganckstraat 35, B-9000 GHENT, Belgium) in accordance with the Treaty of Budapest under number LMG P-13056 on Jun. 21, 1993.

II. Expression Systems

The present invention provides host cells, expression methods and systems for the production and secretion of modified pullulanase in gram-positive microorganisms and gram-negative microorganisms. In one embodiment, a host cell is genetically engineered to comprise nucleic acid encoding a modified pullulanase. In another embodiment, the host cell is genetically engineered to comprise nucleic acid encoding a full length or mature pullulanase, which upon culturing produces a modified pullulanase. In a preferred embodiment, the host cell is a member of the genus *Bacillus* which has been modified to have a mutation or deletion of endogenous proteases.

Inactivation of a Protease in a Host Cell

Producing an expression host cell incapable of producing a naturally occurring protease necessitates the replacement and/or inactivation of the naturally occurring gene from the genome of the host cell. In a preferred embodiment, the mutation is a non-reverting mutation.

One method for mutating nucleic acid encoding a protease is to clone the nucleic acid or part thereof, modify the nucleic acid by site directed mutagenesis and reintroduce the mutated nucleic acid into the cell on a plasmid. By homologous recombination, the mutated gene may be introduced into the chromosome. In the parent host cell, the result is that the naturally occurring-nucleic acid and the mutated nucleic acid are located in tandem on the chromosome. After a second recombination, the modified sequence is left in the chromosome having thereby effectively introduced the mutation into the chromosomal gene for progeny of the parent host cell.

Another method for inactivating the protease proteolytic activity is through deleting the chromosomal gene copy. In a preferred embodiment, the entire gene is deleted, the deletion occurring in such as way as to make reversion impossible. In another preferred embodiment, a partial deletion is produced, provided that the nucleic acid sequence left in the chromosome is too short for homologous recombination with a plasmid encoded metallo-protease gene. In another preferred embodiment, nucleic acid encoding the catalytic amino acid residues are deleted.

Deletion of the naturally occurring microorganism protease can be carried out as follows. A protease gene including its 5' and 3' regions is isolated and inserted into a cloning vector. The coding region of the protease gene is deleted from the vector in vitro, leaving behind a sufficient amount of the 5' and 3' flanking sequences to provide for homologous recombination with the naturally occurring gene in the parent host cell. The vector is then transformed into the host cell. The vector integrates into the chromosome via homologous recombination in the flanking regions. This method leads to a strain in which the protease gene has been deleted.

The vector used in an integration method is preferably a plasmid. A selectable marker may be included to allow for ease of identification of desired recombinant microorganisms. Additionally, as will be appreciated by one of skill in the art, the vector is preferably one which can be selectively integrated into the chromosome. This can be achieved by introducing an inducible origin of replication, for example, a temperature sensitive origin into the plasmid. By growing the transformants at a temperature to which the origin of replication is sensitive, the replication function of the plasmid is inactivated, thereby providing a means for selection of chromosomal integrants. Integrants may be selected for growth at high temperatures in the presence of the selectable marker, such as an antibiotic. Integration mechanisms are described in WO 88/06623.

Integration by the Campbell-type mechanism can take place in the 5' flanking region of the protease gene, resulting in a protease positive strain carrying the entire plasmid vector in the chromosome in the pullulanase locus. Since illegitimate recombination will give different results it will be necessary to determine whether the complete gene has been deleted, such as through nucleic acid sequencing or restriction maps.

Another method of inactivating the naturally occurring protease gene is to mutagenize the chromosomal gene copy by transforming a microorganism with oligonucleotides which are mutagenic. Alternatively, the chromosomal protease gene can be replaced with a mutant gene by homologous recombination.

The present invention encompasses *Bacillus* host cells having protease deletions or mutations, such as deletions or mutations in apr, npr, epr, mpr, isp and/or bpf and/or others known to those of skill in the art. Disclosure relating to deleting protease(s) in the gram-positive microorganism, *Bacillus*, can be found in U.S. patent application Ser. Nos. 5,264,366; 5,585,253; 5,620,880 and European Patent No. EP 0369 817 B1

One assay for the detection of mutants involves growing the *Bacillus* host cell on medium containing a protease substrate and measuring the appearance or lack thereof, of a zone of clearing or halo around the colonies. Host cells which have an inactive protease will exhibit little or no halo around the colonies.

III. Production of Modified Pullulanase

For production of modified pullulanase in a host cell, an expression vector comprising at least one copy of nucleic acid encoding a modified pullulanase, and preferably comprising multiple copies, is transformed into the host cell under conditions suitable for expression of the modified pullulanase. In accordance with the present invention, polynucleotides which encode a modified pullulanase, or fusion proteins or polynucleotide homolog sequences that encode amino acid variants of modified pullulanase (as long as the variant retains the ability to catalyse the hydrolysis of a α-1,6-glucosidic bond), may be used to generate recombinant DNA molecules that direct their expression in host cells. A host cell may be a gram-positive or a gram-negative cell. In one embodiment, the host cell belongs to the genus *Bacillus*. In another embodiment, the *Bacillus* host cell includes *B. subtilis, B. licheniformis, B. lentus, B. brevis, B. stearothermophilus, B. alkalophilus, B. amyloliquefaciens, B. coagulans, B. circulans, B. lautus* and *Bacillus thuringiensis*. In a preferred embodiment, the gram positive host cell is *Bacillus licheniformis*.

As will be understood by those of skill in the art, it may be advantageous to produce polynucleotide sequences possessing non-naturally occurring codons. Codons preferred by a particular gram-positive host cell (Murray E et al (1989) Nuc Acids Res 17:477-508) can be selected, for example, to increase the rate of expression or to produce recombinant RNA transcripts having desirable properties, such as a longer half-life, than transcripts produced from naturally occurring sequence.

Altered pullulanase polynucleotide sequences which may be used in accordance with the invention include deletions, insertions or substitutions of different nucleotide residues resulting in a polynucleotide that encodes the same or a functionally equivalent modified pullulanase. As used herein a "deletion" is defined as a change in either nucleotide or amino acid sequence in which one or more nucleotides or amino acid residues, respectively, are absent.

As used herein an "insertion" or "addition" is that change in a nucleotide or amino acid sequence which has resulted in the addition of one or more nucleotides or amino acid residues, respectively, as compared to the naturally occurring modified pullulanase.

As used herein "substitution" results from the replacement of one or more nucleotides or amino acids by different nucleotides or amino acids, respectively.

The encoded protein may also show deletions, insertions or substitutions of amino acid residues which produce a silent change and result in a functionally equivalent modified pullulanase. Deliberate amino acid substitutions may be made on the basis of similarity in polarity, charge, solubility, hydrophobicity, hydrophilicity, and/or the amphipathic nature of the residues as long as the variant retains the ability to modulate secretion. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine, phenylalanine, and tyrosine.

The polynucleotides encoding a modified pullulanase of the present invention may be engineered in order to modify the cloning, processing and/or expression of the gene product. For example, mutations may be introduced using techniques which are well known in the art, eg, site-directed mutagenesis to insert new restriction sites, to alter glycosylation patterns or to change codon preference, for example.

In one embodiment of the present invention, a polynucleotide encoding a modified pullulanase may be ligated to a heterologous sequence to encode a fusion protein. A fusion protein may also be engineered to contain a cleavage site located between the modified pullulanase nucleotide sequence and the heterologous protein ssequence, so that the modified pullulanase may be cleaved and purified away from the heterologous fusion partner.

IV. Vector Sequences

Expression vectors used in expressing the pullulanases of the present invention in host microorganisms comprise at least one promoter associated with a modified pullulanase, which promoter is functional in the host cell. In one embodiment of the present invention, the promoter is the wild-type promoter for the selected pullulanase and in another embodiment of the present invention, the promoter is heterologous to the pullulanase, but still functional in the host cell. In one embodiment of the present invention, nucleic acid encoding the modified pullulanase is stably integrated into the microorganism genome.

In a preferred embodiment, the expression vector contains a multiple cloning site cassette which preferably comprises at least one restriction endonuclease site unique to the vector, to facilitate ease of nucleic acid manipulation. In a preferred embodiment, the vector also comprises one or more selectable markers. As used herein, the term selectable marker refers to a gene capable of expression in the host microorganism which allows for ease of selection of those hosts containing the vector. Examples of such selectable markers include but are not limited to antibiotics, such as, erythromycin, actinomycin, chloramphenicol and tetracycline.

V. Transformation

A variety of host cells can be used for the production of modified pullulanase including bacterial, fungal, mammalian and insects cells. General transformation procedures are taught in Current Protocols In Molecular Biology (vol. 1, edited by Ausubel et al., John Wiley & Sons, Inc. 1987, Chapter 9) and include calcium phosphate methods, transformation using DEAE-Dextran and electroporation. Plant transformation methods are taught in Rodriquez (WO 95/14099, published May 26, 1995).

In a preferred embodiment, the host cell is a gram-positive microorganism and in another preferred embodiment, the host cell is *Bacillus*. In a further preferred embodiment the *Bacillus* host is *Bacillus licheniformis*. In one embodiment of the present invention, nucleic acid encoding a modified pullulanase of the present invention is introduced into a host cell via an expression vector capable of replicating within the *Bacillus* host cell. Suitable replicating plasmids for *Bacillus* are described in Molecular Biological Methods for *Bacillus*, Ed. Harwood and Cutting, John Wiley & Sons, 1990, hereby expressly incorporated by reference; see chapter 3 on plasmids. Suitable replicating plasmids for *B. subtilis* are listed on page 92.

In another embodiment, nucleic acid encoding a modified pullulanase of the present invention is stably integrated into the host microorganism genome. Preferred host cells are gram-positive host cells. Another preferred host is *Bacillus*. *Bacillus* host cells include *B. subtilis*, *B. licheniformis*, *B. lentus*, *B. brevis*, *B. stearothermophilus*, *B. alkalophilus*, *B. amyloliquefaciens*, *B. coagulans*, *B. circulans*, *B. lautus* and *Bacillus thuringiensis*. A preferred host is *Bacillus subtilis*. Another preferred host is *B. licheniformis*. Several strategies have been described in the literature for the direct cloning of DNA in *Bacillus*. Plasmid marker rescue transformation involves the uptake of a donor plasmid by competent cells carrying a partially homologous resident plasmid (Contente et al., Plasmid 2:555-571 (1979); Haima et al., Mol. Gen. Genet. 223:185-191 (1990); Weinrauch et al., J. Bacteriol. 154(3):1077-1087 (1983); and Weinrauch et al., J. Bacteriol. 169(3):1205-1211 (1987)). The incoming donor plasmid recombines with the homologous region of the resident "helper" plasmid in a process that mimics chromosomal transformation.

Transformation by protoplast transformation is described for *B. subtilis* in Chang and Cohen, (1979) Mol. Gen. Genet 168:111-115; for *B. megaterium* in Vorobjeva et al., (1980) FEMS Microbiol. Letters 7:261-263; for *B. amyloliquefaciens* in Smith et al., (1986) Appl. and Env. Microbiol. 51:634; for *B. thuringiensis* in Fisher et al., (1981) Arch. Microbiol. 139:213-217; for *B. sphaericus* in McDonald (1984) J. Gen. Microbiol. 130:203; and *B. larvae* in Bakhiet et al., (1985, Appl. Environ. Microbiol. 49:577). Mann et al., (1986, Current Microbiol. 13:131-135) report on transformation of *Bacillus* protoplasts and Holubova, (1985) Folia Microbiol. 30:97) disclose methods for introducing DNA into protoplasts using DNA containing liposomes.

VI. Identification of Transformants

Whether a host cell has been transformed with a modified or a naturally occurring gene encoding a pullulanase activity, detection of the presence/absence of marker gene expression can suggest whether the gene of interest is present However, its expression should be confirmed. For example, if the nucleic acid encoding a modified pullulanase is inserted within a marker gene sequence, recombinant cells containing the insert can be identified by the absence of marker gene function. Alternatively, a marker gene can be placed in tandem with nucleic acid encoding the pullulanase under the control of a single promoter. Expression of the marker gene in response to induction or selection usually indicates expression of the pullulanase as well.

Alternatively, host cells which contain the coding sequence for a modified pullulanase and express the protein may be identified by a variety of procedures known to those of skill in the art. These procedures include, but are not limited to, DNA-DNA or DNA-RNA hybridization and protein bioassay or immunoassay techniques which include membrane-based, solution-based, or chip-based technologies for the detection and/or quantification of the nucleic acid or protein.

The presence of the pullulanase polynucleotide sequence in a host microorganism can be detected by DNA-DNA or DNA-RNA hybridization or amplification using probes, portions or fragments of the pullulanase polynucleotide sequences.

VII. Assay of Pullulanase Activity

There are various assays known to those of skill in the art for detecting and measuring pullulanase activity. An enzymatic unit of *B. deramificans* pullulanase (PUN) is defined as the amount of enzyme which, at a pH of 4.5, at a temperature of 60 degrees C. and in the presence of pullulane, catalyses the release of reducing sugars at a rate of 1 µM glucose equivalent per minute.

Pullulanase activity can be measured in the presence or the absence of substrate. In one aspect, pullulanase activity can be measured in the presence of substrate according to the following protocol. 1 ml of a 1% strength solution of pullulane in a 50 nM acetate buffer at pH 4.5 is incubated at 60° C. for 10 minutes. 0.1 ml of a solution of pullulanase corresponding to an activity of between 0.2 and 1 PUN/ml is added thereto. The reaction is stopped after 15 minutes by addition of 0.4 ml of 0.5 M NaOH. The reducing sugars released are analyzed by the method of SOMOGYI-NELSON [J. Biol. Chem., 153 (1944) pages 375-380; and J. Biol. Chem., 160 (1945), pages 61-68].

Another method can be used to analyze the pullulanase. The enzymatic reaction in the presence of pullulane is carried out in accordance with the above test conditions, and is then stopped by addition of sulphuric acid (0.1 N). The hydrolysis products of pullulane are then subjected to HPLC chromatography (HPX-87H column from BIO-RAD; the mobile phase is 10 mM $H_2SO_4$) in order to separate the various constituents. The amount of Maltotriose formed is estimated by measurement of the area of the peak obtained.

The so-called debranching activity, that is to say the hydrolysis of the α-1,6-glucosidic bonds present in amylopectin, can be quantified by the increase in the blue coloration caused, in the presence of iodine, by the release of amylose from amylopectin. The debranching enzymatic activity is measured in accordance with the following protocol. 0.4 ml of a 1% strength amylopectin solution containing a 50 mM acetate buffer at pH 4.5 is incubated at 60° C. for 10 minutes. The reaction is initiated by addition of 0.2 ml of pullulanase, and is stopped after 30 minutes by addition of 0.4 ml of 0.3 M HC1. 0.8 ml of a 0.0025% (v/v) strength solution of iodine is then added to 0.2 ml of this reaction mixture and the optical density is measured at 565 nm.

A preferred method is disclosed in Example IV and relies on a colorimetric method that utilizes a soluble red-pullulan substrate for the determination of pullulanase activity. As the pullulanase enzyme hydrolyzes the substrate, soluble fragments of the dyed substrate are released into the reaction solution. The substrate is then precipitated with an ethanol solution and the supernatant is evaluated for color intensity with spectrophotometer. In this assay, the degree of color intensity is proportional to the enzyme activity.

VIII. Secretion of Recombinant Proteins

Means for determining the levels of secretion of a modified pullulanase in a host microorganism and detecting secreted proteins include, using either polyclonal or monoclonal antibodies specific for the protein. Examples include enzyme-linked immunosorbent assay (ELISA), radioimmunoassay (RIA) and fluorescent activated cell sorting (FACS). These and other assays are described, among other places, in Hampton R et al (1990, Serological Methods, a Laboratory Manual, APS Press, St Paul Minn.) and Maddox D E et al (1983, J Exp Med 158:1211).

A wide variety of labels and conjugation techniques are known by those skilled in the art and can be used in various nucleic and amino acid assays. Means for producing labeled hybridization or PCR probes for detecting specific polynucleotide sequences include oligolabeling, nick translation, end-labeling or PCR amplification using a labeled nucleotide. Alternatively, the nucleotide sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 and incorporated herein by reference.

IX. Purification of Proteins

Host cells transformed with polynucleotide sequences encoding modified pullulanase may be cultured under conditions suitable for the expression and recovery of the pullulanase from cell culture. The protein produced by a recombinant gram-positive host cell comprising a mutation or deletion of endogenous protease activity will be secreted into the culture media. Other recombinant constructions may join the modified pullulanase polynucleotide sequences to a nucleotide sequence encoding a polypeptide domain which will facilitate purification of soluble proteins (Kroll D J et al (1993) DNA Cell Biol 12:441-53).

Such purification facilitating domains include, but are not limited to, metal chelating peptides such as histidine-tryptophan modules that allow purification on immobilized metals (Porath J (1992) Protein Expr Purif 3:263-281), protein A domains that allow purification on immobilized immunoglobulin, and the domain utilized in the FLAGS extension/affinity purification system (Immunex Corp, Seattle Wash.). The inclusion of a cleavable linker sequence such as Factor XA or enterokinase (Invitrogen, San Diego Calif.) between the purification domain and the heterologous protein can be used to facilitate purification.

X. Uses of the Present Invention

Modified pullulanase

A modified pullulanase of the present invention finds use in various industries including the food industry, the pharmaceuticals industry and the chemical industry. A modified pullulanase can be used in baking as an "anti-staling" agent, that is to say as an additive to prevent bread becoming stale during storage, or in brewing during production of low-calorie beers. The pullulanase can also be used in the preparation of low-calorie foods in which amylose is used as a substitute for fats. The pullulanase can be used, for example, to clarify fruit juices.

For food applications, the pullulanase can be immobilized on a support. The techniques for immobilization of enzymes are well known to the expert.

The pullulanase can also be used to hydrolyse amylopectin and to form oligosaccharides starting from this amylopectin. The pullulanase can also be used to form tetraholosides starting from maltose.

The pullulanase can also be used to condense mono- or oligo-saccharides, creating bonds of the alpha-1,6 type. The pullulanase can be used for liquefaction of starch.

A modified pullulanase can be used in the same manner as its respective unmodified form. A modified pullulanase, which in unmodified form has activity under alkaline conditions, will retain activity under alkaline conditions. A modified pullulanase which in unmodified form has activity under acidic conditions, will retain activity under acidic conditions. A particular modified pullulanase will be formulated according to the intended uses. Stabilizers or preservatives can also be added to the enzymatic compositions comprising a modified pullulanase. For example, a modified pullulanase can be stabilized by addition of propylene glycol, ethylene glycol, glycerol, starch, pullulane, a sugar, such as glucose or sorbitol, a salt, such as sodium chloride, calcium chloride, potassium sorbate, and sodium benzoate, or a mixture of two or more of these products. The enzymatic compositions according to the invention can also comprise one or more other enzymes. Such enzymes include but are not limited to glucoamylase, alpha-amylase, beta-amylase, alpha-glucosidase, isoamylase, cyclomaltodextrin, glucotransferase, beta-glucanase, glucose isomerase, saccharifying enzymes, and enzymes which cleave glucosidic bonds or a mixture of two or more of these. In a preferred embodiment, the enzymatic composition comprises a modified pullulanase of the present invention at 80% and a glucoamylase at 20%.

The manner and method of carrying out the present invention may be more fully understood by those of skill in the art by reference to the following examples, which examples are not intended in any manner to limit the scope of the present invention or of the claims directed thereto. All references and patent publications disclosed herein are hereby incorporated by reference.

EXAMPLES

Example I

Example I illustrates the production of a modified pullulanase as described herein. The nucleic acid sequence encoding a pullulanase is modified by recombinant DNA techniques such as standard PCR primer-directed enzymatic amplification of DNA with a thermostable DNA polymerase. (Saiki, R. K., et al., 1988, Science 239:487-491.) and PCR fusion techniques (Fleming, A. B., et al. *Appl. Environ. Microbiol.* 61, 3775-3780). DNA encoding the desired modified pullulanase is fused to the C-terminus of a signal sequence, preferably a host microorganism signal sequence. This construct is cloned and transformed into a host cell, such as, *B. subtilis* or *B. licheniformis*, and cultured under standard fermentation conditions. The modified pullulanase is purified from the fermentation broth and assayed for activity.

Example II

Example II describes the modified forms of pullulanase obtained upon culturing the recombinant *B. licheniformis* host cell comprising nucleic acid encoding a mature *B. deramificans* pullulanase wherein the host cell has a deletion of the Carlsburg and endo GluC proteases. The *B. licheniformis* was cultured under standard fermentation conditions in a complex media. The fermentation broth was subjected to standard HPCL analysis and the results are shown in FIGS. 3A-3C which illustrate a timecourse of the various species of modified pullulanase formed during the fermentation process. Peak 1 designates the mature *B. deramificans* pullulanase having a molecular weight of 105 kD; peak 2 designates the modified pullulanase which has deletion of 102 amino acids from the amino terminus of mature *B. deramificans* pullulanase; and peak 3 designates the modified pullulanase which has a deletion of 98 amino acids from the amino terminus as measured by standard HPLC analysis. The modified pullulanase species which has an additional amino acid on the mature sequence is not detectable by HPLC analysis but was detected upon nucleic acid sequencing. FIGS. 3A-3C illustrate that over fermentation time, Peak 1 corresponding to the mature *B. deramificans* pullulanase decreases while Peaks 2 and 3 increase. FIGS. 4A-4D illustrate the stability of the modified pullulanase produced upon fermentation of *B. licheniformis* having a deletion of the Carlsburg and endo-GluC proteases. *B. licheniformis* comprising nucleic acid encoding a mature *B. deramificans* was cultured under conditions suitable for the expression and secretion of the modified pullulanase and the fermentation broth was adjusted to a pH of 4.5, 5.5 and 6.5 at room temperature. The modified pullulanase was most stable at a pH of 4.5.

Example III

Example III describes the saccharification process comparing enzymatic compositions comprising different percentages of pullulanase. Enzymatic compositions comprising either 20% glucoamylase:80% modified pullulanase (20:80) activity or 75% glucoamylase:25% pullulanase activity (75:25) were tested in saccharification processes at a concentration of 0.550, 0.635 and 0.718 liters of enzymatic composition per metric ton of dissolved solids. As shown in FIGS. 5A-5C, an enzymatic composition comprising 20% glucoamylase and 80% pullulanase activity is able to increase the final glucose yield without an increase in undesirable disaccharide formation. Furthermore, the absolute concentration of the 20:80 enzyme composition can be increased without the undesirable increase in disaccharide formation that is seen with the 75:25 enzyme composition or glucoamylase alone.

Example IV

Example IV describes an assay for the determination of activity of a modified pullulanase of the present invention. This assay is based on a colorimetric method that utilizes a soluble red-pullulan substrate for the determination of pullulanase activity.

Reagent Preparation

A 200 mM Sodium Acetate buffer pH 5.0 w/Acarbose (density~1.010) was prepared by weighing out 16.406 g of anhydrous Sodium acetate or 27.21 g of Sodium acetate trihydrate and dissolving it in 900 mis of deionized water (DI) in 1 L graduated cylinder by stirring with a magnetic stir bar. The pH was adjusted to 5.0 with glacial acetic acid. 0.300 g of Acarbose was added to the solution and allowed to dissolve. The volume was brought up to 1000 mL with DI water and mixed.

2% Red Pullulan Substrate Preparation 1.00 g of Red Pullulan substrate was weighed out and dissolved in 50 mL of sodium acetate buffer by stirring with a magnetic stir bar for approximately 20-30 minutes. This solution is stable for two weeks stored at 4° C.

Preparation of a Working Standard

Using positive displacement pipettes a 1:10 dilution of the Pullulanase Standard was prepared. The assigned activity of the standard was 195.9 ASPU/ml. The following working concentrations were prepared from the standard from the 1:10 stock dilution.

Sample Preparation

For a control, Optimax L-300 MA7EC191 PU B13-19A available from Genencor International was used. The control was diluted 1:1000 in sodium acetate buffer. All samples were diluted in sodium acetate buffer to obtain final reaction absorbances that fall on the calibration curve. The sample was brought to room temperature. A minimum of 100 ul of sample was used for the initial dilution.

Assay Procedure 250 ul of each standard working concentration, control and sample was placed into two appropriately labeled microcentrifuge tubes. To each tube 250 ul of 2% substrate solution was added with a repeater pipette and a 12.5 ml Combitip set on 1. The samples were Vortexed for 3 seconds and incubated at 40° C. for 20 minutes. The samples were remove from the water bath and immediately 1.0 ml of 95% EtOH was added to the samples in the same order as above. A repeater pipette and a 12.5 or 50 ml Combitip set on 4 or 1, was used. The samples were vortexed for 3 seconds. The samples were incubated at room temperature for 5-10 minutes, then centrifuged for ten minutes in a benchtop centrifuge. The supernatant of the standards and samples were read in a spectrophotometer at 510 nm using 1.5 mL cuvettes. (The spectrophotometer was zeroed with 95% EtOH)

Calculations

Using the standard concentrations and correlating absorbances (subtracting the blank absorbance), a calibration curve is developed with a computer spreadsheet, programmable calculator, or graph paper. The curve should be linear over the range of the standard concentrations with a correlation coefficient (r) of 0.998 or greater. The precision of the assay should fall between 5-10% CV. For liquids: u/ml=(u/ml from standard curve)*(sample dilution)

The invention claimed is:

1. An isolated or purified nucleic acid comprising a polynucleotide sequence encoding a truncated pullulanase, wherein said truncated pullulanase comprises a deletion of either 98 or 102 amino acids from the amino terminus of the mature form of the *Bacillus deramificans* pullulanase of SEQ ID NO:2, wherein said pullulanase catalyzes the hydrolysis of an alpha-1,6-glucosidic bond.

2. An isolated or purified polynucleotide encoding a truncated pullulanase, wherein said truncated pullulanase comprises a deletion of either 98 or 102 amino acids from the amino terminus of the mature form of the *Bacillus deramificans* pullulanase of SEQ ID NO:2, and wherein said pullulanase catalyzes the hydrolysis of an alpha-1,6-glucosidic bond, wherein said polynucleotide has at least 95% identity to SEQ ID NO:1.

3. The nucleic acid of claim 1 having the polynucleotide sequence of SEQ ID NO: 1.

4. An expression vector comprising the nucleic acid of claim 1.

5. A host microorganism comprising the expression vector of claim 4.

6. The host microorganism of claim 5 wherein said microorganism is a *Bacillus*.

7. The host microorganism of claim 6 wherein said *Bacillus* is selected from the group consisting of *B. subtilis, B. licheniformis, B. lentus, B. brevis, B. stearothermophilus, B. alkalophilus, B. amyloliquefaciens, B. coagulans, B. circulans, B. lautus* and *B. thuringiensis.*

8. A method for the production of a truncated pullulanase in a host cell comprising the steps of:
a) transforming a host cell with an expression vector comprising a nucleic acid encoding a truncated pullulanase, wherein said pullulanase comprises a deletion of either 98 or 102 amino acids from the amino terminus of the mature form of the *Bacillus deramificans* pullulanase of SEQ ID NO:2, wherein said pullulanase catalyzes the hydrolysis of an alpha-1,6-glucosidic bond; and
b) culturing the host cell under conditions suitable for the production of the truncated pullulanase.

9. The method of claim 8 further comprising recovering the truncated pullulanase.

10. The method of claim 8 wherein the host cell is a *Bacillus* selected from the group consisting of *B. subtilis, B. licheniformis, B. lentus, B. brevis, B. stearothermophilus, B. alkalophilus, B. amyloliquefaciens, B. coagulans, B. circulans, B. lautus* and *B. thuringiensis.*

11. An isolated or purified *Bacillus licheniformis* comprising a nucleic acid encoding a truncated pullulanase, wherein said truncated pullulanase catalyzes the hydrolysis of an alpha-1,6-glucosidic bond and is selected from the group consisting of a deletion of 98 amino acids, a deletion of 102 amino acids, a deletion of 200 amino acids, and a deletion of 300 amino acids from the amino terminus of the mature form of the *Bacillus deramificans* pullulanase of SEQ ID NO:2, wherein said *Bacillus licheniformis* further comprises a first gene encoding Carlsberg protease and a second gene encoding endo Glu C protease, wherein at least one of said first gene or said second gene has been altered to eliminate protease activity.

12. An isolated or purified nucleic acid comprising a polynucleotide sequence encoding a truncated pullulanase, wherein said truncated pullulanase comprises a deletion of either 98 or 102 amino acids from the amino terminus of the mature form of the *Bacillus deramificans* pullulanase of SEQ ID NO:2, wherein said pullulanase catalyzes the hydrolysis of an alpha-1,6-glucosidic bond, and wherein said *Bacillus deramificans* has the biological deposit number T89.117D in the Belgian Coordinated Collections of Microorganisms at the University of Ghent, Laboratory of Microbiology (LMG culture collection).

13. An expression vector comprising the nucleic acid of claim 2.

14. An isolated or purified nucleic acid comprising a polynucleotide sequence encoding a truncated pullulanase, wherein said truncated pullulanase comprises a deletion of 200 amino acids from the amino terminus of the mature form of the *Bacillus deramificans* pullulanase of SEQ ID NO:2, wherein said pullulanase catalyzes the hydrolysis of an alpha-1,6-glucosidic bond.

15. An isolated or purified nucleic acid comprising a polynucleotide sequence encoding a truncated pullulanase, wherein said truncated pullulanase comprises a deletion of 300 amino acids from the amino terminus of the mature form of the *Bacillus deramificans* pullulanase of SEQ ID NO:2, wherein said pullulanase catalyzes the hydrolysis of an alpha-1,6-glucosidic bond.

16. The method according to claim 8, wherein the truncated pullulanase has the amino acid sequence of SEQ ID NO: 2 beginning at amino acid residue 128, a glutamic acid.

17. The method according to claim 8, wherein the truncated pullulanase has the amino acid sequence of SEQ ID NO: 2 beginning at amino acid residue 132, a glutamic acid.

18. A method for the production of a truncated pullulanase in a *Bacillus licheniformis* host cell comprising the steps of:
a) transforming a *Bacillus licheniformis* host cell with a nucleic acid encoding a truncated pullulanase, wherein said truncated pullulanase comprises a deletion of either 98 or 102 amino acids from the amino terminus of the mature form of the *Bacillus deramificans* pullulanase of SEQ ID NO:2, wherein said pullulanase catalyzes the hydrolysis of an alpha-1,6-glucosidic bond; and b) culturing the host cell under conditions suitable for the production of the truncated pullulanase.

19. The method according to claim 18 further comprising recovering the truncated pullulanase.

20. The method according to claim 18, wherein the truncated pullulanase has the amino acid sequence of SEQ ID NO: 2 beginning at amino acid residue 128, a glutamic acid.

21. The method according to claim 18, wherein the truncated pullulanase has the amino acid sequence of SEQ ID NO: 2 beginning at amino acid residue 132, a glutamic acid.

22. A *Bacillus licheniformis* host cell which has been transformed with the nucleic acid of claim 1.

23. A method for the production of a truncated pullulanase in a host cell, comprising culturing said host cell under conditions suitable for the production of the truncated pullulanase, wherein said host cell has been transformed with an expression vector comprising a polynucleotide sequence encoding a truncated pullulanase, wherein said truncated pullulanase comprises a deletion of either 98 or 102 amino acids from the amino terminus of the mature form of the *Bacillus deramificans* pullulanase of SEQ ID NO:2, wherein said pullulanase catalyzes the hydrolysis of an alpha-1,6-glucosidic bond.

24. A method according to claim 23, wherein said host cell is a *Bacillus licheniformis* host cell.

25. A method for the production of a truncated pullulanase in a host cell, comprising culturing said host cell under conditions suitable for the production of the truncated pullulanase, wherein said host cell has been transformed with an expression vector comprising a polynucleotide sequence encoding a truncated pullulanase, wherein said truncated pullulanase comprises a deletion of 200 amino acids from the amino terminus of the mature form of the *Bacillus deramificans* pullulanase of SEQ ID NO:2, wherein said pullulanase catalyzes the hydrolysis of an alpha-1,6-glucosidic bond.

26. A method according to claim 24, wherein said host cell is a *Bacillus licheniformis* host cell.

27. A method for the production of a truncated pullulanase in a host cell, comprising culturing said host cell under conditions suitable for the production of the truncated pullulanase, wherein said host cell has been transformed with an expression vector comprising a polynucleotide sequence encoding a truncated pullulanase, wherein said truncated pullulanase comprises a deletion of 300 amino acids from the amino terminus of the mature form of the *Bacillus deramificans* pullulanase of SEQ ID NO:2, wherein said pullulanase catalyzes the hydrolysis of an alpha-1,6-glucosidic bond.

28. A method according to claim 27, wherein said host cell is a *Bacillus licheniformis* host cell.

29. The nucleic acid according to claim 1, wherein the truncated pullulanase has the amino acid sequence of SEQ ID NO:2 beginning at amino acid residue 128, a glutamic acid.

30. The nucleic acid according to claim 1, wherein the truncated pullulanase has the amino acid sequence of SEQ ID NO:2 beginning at amino acid residue 132, a glutamic acid.

* * * * *

SEQUENCE LISTING

<160> NUMBER OF SEQ ID NOS: 9

<210> SEQ ID NO 1
<211> LENGTH: 2794
<212> TYPE: DNA
<213> ORGANISM: Bacillus deramificans
<220> FEATURE:
<221> NAME/KEY: misc_feature
<222> LOCATION: (1)...(2794)
<223> OTHER INFORMATION: n = A, T, C, or G

<400> SEQUENCE: 1

| | | | | | |
|---|---|---|---|---|---|
| gatgggaaca | cgacaacgat | cattgtccac | tattttttgcc | ctgctggtga | ttatcaacct | 60 |
| tggagtctat | ggatgtggcc | aaaagacgga | ggtggggctg | aatacgattt | caatcaaccg | 120 |
| gctgactctt | ttggagctgt | tgcaagtgct | gatattccag | gaaacccaag | tcaggtagga | 180 |
| attatcgttc | gcactcaaga | ttggaccaaa | gatgtgagcg | ctgaccgcta | catagattta | 240 |
| agcaaaggaa | atgaggtgtg | gcttgtagaa | ggaaacagcc | aaatttttta | taatgaaaaa | 300 |
| gatgctgagg | atgcagctaa | acccgctgta | agcaacgctt | atttagatgc | ttcaaaccag | 360 |
| gtgctggtta | aacttagcca | gccgttaact | cttggggaag | gnnnaagcgg | ctttacggtt | 420 |
| catgacgaca | cagcaaataa | ggatattcca | gtgacatctg | tgaaggatgc | aagtcttggt | 480 |
| caagatgtaa | ccgctgtttt | ggcaggtacc | ttccaacata | tttttggagg | ttccgattgg | 540 |
| gcacctgata | atcacagtac | tttattaaaa | aaggtgacta | acaatctcta | tcaattctca | 600 |
| ggagatcttc | ctgaaggaaa | ctaccaatat | aaagtggctt | taaatgatag | ctggaataat | 660 |
| ccgagttacc | catctgacaa | cattaattta | acagtccctg | ccggcggtgc | acacgtcact | 720 |
| ttttcgtata | ttccgtccac | tcatgcagtc | tatgacacaa | ttaataatcc | taatgcggat | 780 |
| ttacaagtag | aaagcggggt | taaaacggat | ctcgtgacgg | ttactctagg | ggaagatcca | 840 |
| gatgtgagcc | atactctgtc | cattcaaaca | gatggctatc | aggcaaagca | ggtgatacct | 900 |
| cgtaatgtgc | ttaattcatc | acagtactac | tattcaggag | atgatcttgg | gaataccta t | 960 |
| acacagaaag | caacaacctt | taaagtctgg | gcaccaactt | ctactcaagt | aaatgttctt | 1020 |
| ctttatgaca | gtgcaacggg | ttctgtaaca | aaaatcgtac | ctatgacggc | atcgggccat | 1080 |
| ggtgtgtggg | aagcaacggt | taatcaaaac | cttgaaaatt | ggtattacat | gtatgaggta | 1140 |
| acaggccaag | gctctacccg | aacggctgtt | gatccttatg | caactgcgat | tgcaccaaat | 1200 |
| ggaacgagag | gcatgattgt | ggacctggct | aaaacagatc | ctgctggctg | gaacagtgat | 1260 |
| aaacatatta | cgccaaagaa | tatagaagat | gaggtcatct | atgaaatgga | tgtccgtgac | 1320 |
| ttttccattg | accctaattc | gggtatgaaa | aataaaggga | gtatttggc | tcttacagaa | 1380 |
| aaaggaacaa | agggccctga | caacgtaaag | acggggatag | attccttaaa | caacttggg | 1440 |
| attactcatg | ttcagcttat | gcctgttttc | gcatctaaca | gtgtcgatga | aactgatcca | 1500 |
| acccaagata | attggggtta | tgaccctcgc | aactatgatg | ttcctgaagg | gcagtatgct | 1560 |
| acaaatgcga | atggtaatgc | tcgtataaaa | gagtttaagg | aaatggttct | ttcactccat | 1620 |
| cgtgaacaca | ttggggttaa | catggatgtt | gtctataatc | atacctttgc | cacgcaaatc | 1680 |
| tctgacttcg | ataaaattgt | accagaatat | tattaccgta | cgatgatcca | ggtaattata | 1740 |
| ccaacggatc | aggtactgga | aatgaaattg | cangcngaaa | ggccaatggt | tcaaaaattt | 1800 |
| attattgatt | cccttaagta | ttgggtcaat | gagtatcata | ttgacggctt | ccgttttgac | 1860 |
| ttaatggcgc | tgcttggaaa | agacacgatg | tccaaagctg | cctcggagct | tcatgctatt | 1920 |

-continued

```
aatccaggaa ttgcacttta cggtgagcca tggacgggtg gaacctctgc actgccagat    1980
gatcagcttc tgacaaaagg agctcaaaaa ggcatgggag tagcggtgtt taatgacaat    2040
ttacgaaacg cgttggacgg caatgtcttt gattcttccg ctcaaggttt tgcgacaggt    2100
gcaacaggct taactgatgc aattaagaat ggcgttgagg ggagtattaa tgactttacc    2160
tcttcaccag gtgagacaat taactatgtc acaagtcatg ataactacac cctttgggac    2220
aaaatagccc taagcaatcc taatgattcc gaagcggatc ggattaaaat ggatgaactc    2280
gcacaagcag ttgttatgac ctcacaaggc gttccattca tgcaaggcgg ggaagaaatg    2340
cttcgtanaa aaggcggcaa cgacaatagt tataatgcag gcgatgcggt caatgagttt    2400
gattggagca ggaaagctca atatccagat gttttcaact attatagcgg gctaatccac    2460
cttcgtcttg atcacccagc cttccgcatg acgacagcta atgaaatcaa tagccacctc    2520
caattcctaa atagtccaga gaacacagtg gcctatgaat taactgatca tgttaataaa    2580
gacaaatggg gaaatatcat tgttgtttat aacccaaata aaactgtagc aaccatcaat    2640
ttgccgagcg ggaaatgggc aatcaatgct acgagcggta aggtaggaga atccacccct    2700
ggtcaagcag agggaagtgt ccaagtacca ggtatatcta tgatgatcct tcatcaagag    2760
gtaagcccag accacggtaa aaagtaatag aaaa                                2794
```

```
<210> SEQ ID NO 2
<211> LENGTH: 956
<212> TYPE: PRT
<213> ORGANISM: Bacillus deramificans
<220> FEATURE:
<221> NAME/KEY: VARIANT
<222> LOCATION: (1)...(956)
<223> OTHER INFORMATION: Xaa = Any Amino Acid

<400> SEQUENCE: 2
```

Met Ala Lys Lys Leu Ile Tyr Val Cys Leu Ser Val Cys Leu Val Leu
 1               5                  10                  15

Thr Trp Ala Phe Asn Val Lys Gly Gln Ser Ala His Ala Asp Gly Asn
            20                  25                  30

Thr Thr Thr Ile Ile Val His Tyr Phe Cys Pro Ala Gly Asp Tyr Gln
        35                  40                  45

Pro Trp Ser Leu Trp Met Trp Pro Lys Asp Gly Gly Ala Glu Tyr
    50                  55                  60

Asp Phe Asn Gln Pro Ala Asp Ser Phe Gly Ala Val Ala Ser Ala Asp
65                  70                  75                  80

Ile Pro Gly Asn Pro Ser Gln Val Gly Ile Ile Val Arg Thr Gln Asp
                85                  90                  95

Trp Thr Lys Asp Val Ser Ala Asp Arg Tyr Ile Asp Leu Ser Lys Gly
            100                 105                 110

Asn Glu Val Trp Leu Val Glu Gly Asn Ser Gln Ile Phe Tyr Asn Glu
        115                 120                 125

Lys Asp Ala Glu Asp Ala Ala Lys Pro Ala Val Ser Asn Ala Tyr Leu
    130                 135                 140

Asp Ala Ser Asn Gln Val Leu Val Lys Leu Ser Gln Pro Leu Thr Leu
145                 150                 155                 160

Gly Glu Gly Xaa Ser Gly Phe Thr Val His Asp Thr Ala Asn Lys
                165                 170                 175

Asp Ile Pro Val Thr Ser Val Lys Asp Ala Ser Leu Gly Gln Asp Val
            180                 185                 190

-continued

Thr Ala Val Leu Ala Gly Thr Phe Gln His Ile Phe Gly Gly Ser Asp
            195                 200                 205

Trp Ala Pro Asp Asn His Ser Thr Leu Leu Lys Lys Val Thr Asn Asn
        210                 215                 220

Leu Tyr Gln Phe Ser Gly Asp Leu Pro Glu Gly Asn Tyr Gln Tyr Lys
225                 230                 235                 240

Val Ala Leu Asn Asp Ser Trp Asn Asn Ser Tyr Pro Ser Asp Asn Ile
                245                 250                 255

Asn Leu Thr Val Pro Ala Gly Gly Ala His Val Thr Phe Ser Tyr Ile
            260                 265                 270

Pro Ser Thr His Ala Val Tyr Asp Thr Ile Asn Asn Pro Asn Ala Asp
        275                 280                 285

Leu Gln Val Glu Ser Gly Val Lys Thr Asp Leu Val Thr Val Thr Leu
290                 295                 300

Gly Glu Asp Pro Asp Val Ser His Thr Leu Ser Ile Gln Thr Asp Gly
305                 310                 315                 320

Tyr Gln Ala Lys Gln Val Ile Pro Arg Asn Val Leu Asn Ser Ser Gln
                325                 330                 335

Tyr Tyr Tyr Ser Gly Asp Asp Leu Gly Asn Thr Tyr Thr Gln Lys Ala
            340                 345                 350

Thr Thr Phe Lys Val Trp Ala Pro Thr Ser Thr Gln Val Asn Val Leu
        355                 360                 365

Leu Tyr Asp Ser Ala Thr Gly Ser Val Thr Lys Ile Val Pro Met Thr
    370                 375                 380

Ala Ser Gly His Gly Val Trp Glu Ala Thr Val Asn Gln Asn Leu Glu
385                 390                 395                 400

Asn Trp Tyr Tyr Met Tyr Glu Val Thr Gly Gln Gly Ser Thr Arg Thr
                405                 410                 415

Ala Val Asp Pro Tyr Ala Thr Ala Ile Ala Pro Asn Gly Thr Arg Gly
            420                 425                 430

Met Ile Val Asp Leu Ala Lys Thr Asp Pro Ala Gly Trp Asn Ser Asp
        435                 440                 445

Lys His Ile Thr Pro Lys Asn Ile Glu Asp Glu Val Ile Tyr Glu Met
    450                 455                 460

Asp Val Arg Asp Phe Ser Ile Asp Pro Asn Ser Gly Met Lys Asn Lys
465                 470                 475                 480

Gly Lys Tyr Leu Ala Leu Thr Glu Lys Gly Thr Lys Gly Pro Asp Asn
                485                 490                 495

Val Lys Thr Gly Ile Asp Ser Leu Lys Gln Leu Gly Ile Thr His Val
            500                 505                 510

Gln Leu Met Pro Val Phe Ala Ser Asn Ser Val Asp Glu Thr Asp Pro
        515                 520                 525

Thr Gln Asp Asn Trp Gly Tyr Asp Pro Arg Asn Tyr Asp Val Pro Glu
    530                 535                 540

Gly Gln Tyr Ala Thr Asn Ala Asn Gly Asn Ala Arg Ile Lys Glu Phe
545                 550                 555                 560

Lys Glu Met Val Leu Ser Leu His Arg Glu His Ile Gly Val Asn Met
                565                 570                 575

Asp Val Val Tyr Asn His Thr Phe Ala Thr Gln Ile Ser Asp Phe Asp
            580                 585                 590

Lys Ile Val Pro Glu Tyr Tyr Tyr Arg Thr Met Ile Gln Val Ile Ile
        595                 600                 605

Pro Thr Asp Gln Val Leu Glu Met Lys Leu Xaa Ala Glu Arg Pro Met

```
                610                 615                 620
Val Gln Lys Phe Ile Ile Asp Ser Leu Lys Tyr Trp Val Asn Glu Tyr
625                 630                 635                 640

His Ile Asp Gly Phe Arg Phe Asp Leu Met Ala Leu Leu Gly Lys Asp
                645                 650                 655

Thr Met Ser Lys Ala Ala Ser Glu Leu His Ala Ile Asn Pro Gly Ile
                660                 665                 670

Ala Leu Tyr Gly Glu Pro Trp Thr Gly Gly Thr Ser Ala Leu Pro Asp
                675                 680                 685

Asp Gln Leu Leu Thr Lys Gly Ala Gln Lys Gly Met Gly Val Ala Val
690                 695                 700

Phe Asn Asp Asn Leu Arg Asn Ala Leu Asp Gly Asn Val Phe Asp Ser
705                 710                 715                 720

Ser Ala Gln Gly Phe Ala Thr Gly Ala Thr Gly Leu Thr Asp Ala Ile
                725                 730                 735

Lys Asn Gly Val Glu Gly Ser Ile Asn Asp Phe Thr Ser Ser Pro Gly
                740                 745                 750

Glu Thr Ile Asn Tyr Val Thr Ser His Asp Asn Tyr Thr Leu Trp Asp
                755                 760                 765

Lys Ile Ala Leu Ser Asn Pro Asn Asp Ser Glu Ala Asp Arg Ile Lys
770                 775                 780

Met Asp Glu Leu Ala Gln Ala Val Val Met Thr Ser Gln Gly Val Pro
785                 790                 795                 800

Phe Met Gln Gly Gly Glu Glu Met Leu Arg Xaa Lys Gly Gly Asn Asp
                805                 810                 815

Asn Ser Tyr Asn Ala Gly Asp Ala Val Asn Glu Phe Asp Trp Ser Arg
                820                 825                 830

Lys Ala Gln Tyr Pro Asp Val Phe Asn Tyr Tyr Ser Gly Leu Ile His
                835                 840                 845

Leu Arg Leu Asp His Pro Ala Phe Arg Met Thr Thr Ala Asn Glu Ile
850                 855                 860

Asn Ser His Leu Gln Phe Leu Asn Ser Pro Glu Asn Thr Val Ala Tyr
865                 870                 875                 880

Glu Leu Thr Asp His Val Asn Lys Asp Lys Trp Gly Asn Ile Ile Val
                885                 890                 895

Val Tyr Asn Pro Asn Lys Thr Val Ala Thr Ile Asn Leu Pro Ser Gly
                900                 905                 910

Lys Trp Ala Ile Asn Ala Thr Ser Gly Lys Val Gly Glu Ser Thr Leu
                915                 920                 925

Gly Gln Ala Glu Gly Ser Val Gln Val Pro Gly Ile Ser Met Met Ile
930                 935                 940

Leu His Gln Glu Val Ser Pro Asp His Gly Lys Lys
945                 950                 955

<210> SEQ ID NO 3
<211> LENGTH: 718
<212> TYPE: PRT
<213> ORGANISM: Bacillus subtilis

<400> SEQUENCE: 3

Met Val Ser Ile Arg Arg Ser Phe Glu Ala Tyr Val Asp Asp Met Asn
  1               5                  10                  15

Ile Ile Thr Val Leu Ile Pro Ala Glu Gln Lys Glu Ile Met Thr Pro
                 20                  25                  30
```

-continued

```
Pro Phe Arg Leu Glu Thr Glu Ile Thr Asp Phe Pro Leu Ala Val Arg
        35                  40                  45
Glu Glu Tyr Ser Leu Glu Ala Lys Tyr Lys Tyr Val Cys Val Ser Asp
    50                  55                  60
His Pro Val Thr Phe Gly Lys Ile His Cys Val Arg Ala Ser Ser Gly
 65                  70                  75                  80
His Lys Thr Asp Leu Gln Ile Gly Ala Val Ile Arg Thr Ala Ala Phe
                85                  90                  95
Asp Asp Glu Phe Tyr Tyr Asp Gly Glu Leu Gly Ala Val Tyr Thr Ala
               100                 105                 110
Asp His Thr Val Phe Lys Val Trp Ala Pro Ala Ala Thr Ser Ala Ala
               115                 120                 125
Val Lys Leu Ser His Pro Asn Lys Ser Gly Arg Thr Phe Gln Met Thr
130                 135                 140
Arg Leu Glu Lys Gly Val Tyr Ala Val Thr Val Thr Gly Asp Leu His
145                 150                 155                 160
Gly Tyr Glu Tyr Leu Phe Cys Ile Cys Asn Asn Ser Glu Trp Met Glu
                165                 170                 175
Thr Val Asp Gln Tyr Ala Lys Ala Val Thr Val Asn Gly Glu Lys Gly
               180                 185                 190
Val Val Leu Arg Pro Asp Gln Met Lys Trp Thr Ala Pro Leu Lys Pro
            195                 200                 205
Phe Ser His Pro Val Asp Ala Val Ile Tyr Glu Thr His Leu Arg Asp
            210                 215                 220
Phe Ser Ile His Glu Asn Ser Gly Met Ile Asn Lys Gly Lys Tyr Leu
225                 230                 235                 240
Ala Leu Thr Glu Thr Asp Thr Gln Thr Ala Asn Gly Ser Ser Ser Gly
                245                 250                 255
Leu Ala Tyr Val Lys Glu Leu Gly Val Thr His Val Glu Leu Leu Pro
               260                 265                 270
Val Asn Asp Phe Ala Gly Val Asp Glu Glu Lys Pro Leu Asp Ala Tyr
            275                 280                 285
Asn Trp Gly Tyr Asn Pro Leu His Phe Phe Ala Pro Glu Gly Ser Tyr
            290                 295                 300
Ala Ser Asn Pro His Asp Pro Gln Thr Arg Lys Thr Glu Leu Lys Gln
305                 310                 315                 320
Met Ile Asn Thr Leu His Gln His Gly Leu Arg Val Ile Leu Asp Val
                325                 330                 335
Val Phe Asn His Val Tyr Lys Arg Glu Asn Ser Pro Phe Glu Lys Thr
            340                 345                 350
Val Pro Gly Tyr Phe Arg His Asp Glu Cys Gly Met Pro Ser Asn
            355                 360                 365
Gly Thr Gly Val Gly Asn Asp Ile Ala Ser Glu Arg Arg Met Ala Arg
    370                 375                 380
Lys Phe Ile Ala Asp Cys Val Val Tyr Trp Leu Glu Glu Tyr Asn Val
385                 390                 395                 400
Asp Gly Phe Arg Phe Asp Leu Leu Gly Ile Leu Asp Ile Asp Thr Val
                405                 410                 415
Leu Tyr Met Lys Glu Lys Ala Thr Lys Ala Lys Pro Gly Ile Leu Leu
            420                 425                 430
Phe Gly Glu Gly Trp Asp Leu Ala Thr Pro Leu Pro His Glu Gln Lys
        435                 440                 445
Ala Ala Leu Ala Asn Ala Pro Arg Met Pro Gly Ile Gly Phe Phe Asn
```

```
            450                 455                 460
Asp Met Phe Arg Asp Ala Val Lys Gly Asn Thr Phe His Leu Lys Ala
465                 470                 475                 480

Thr Gly Phe Ala Leu Gly Asn Gly Glu Ser Ala Gln Ala Val Met His
                485                 490                 495

Gly Ile Ala Gly Ser Ser Gly Trp Lys Ala Leu Ala Pro Ile Val Pro
            500                 505                 510

Glu Pro Ser Gln Ser Ile Asn Tyr Val Glu Ser His Asp Asn His Thr
        515                 520                 525

Phe Trp Asp Lys Met Ser Phe Ala Leu Pro Gln Glu Asn Asp Ser Arg
    530                 535                 540

Lys Arg Ser Arg Gln Arg Leu Ala Val Ala Ile Ile Leu Leu Ala Gln
545                 550                 555                 560

Gly Val Pro Phe Ile His Ser Gly Gln Glu Phe Phe Arg Thr Lys Gln
                565                 570                 575

Gly Val Glu Asn Ser Tyr Gln Ser Ser Asp Ser Ile Asn Gln Leu Asp
            580                 585                 590

Trp Asp Arg Arg Glu Thr Phe Lys Glu Asp Val His Tyr Ile Arg Arg
        595                 600                 605

Leu Ile Ser Leu Arg Lys Ala His Pro Ala Phe Arg Leu Arg Ser Ala
    610                 615                 620

Ala Asp Ile Gln Arg His Leu Glu Cys Leu Thr Leu Lys Glu His Leu
625                 630                 635                 640

Ile Ala Tyr Arg Leu Tyr Asp Leu Asp Glu Val Asp Glu Trp Lys Asp
                645                 650                 655

Ile Ile Val Ile His His Ala Ser Pro Asp Ser Val Glu Trp Arg Leu
            660                 665                 670

Pro Asn Asp Ile Pro Tyr Arg Leu Leu Cys Asp Pro Ser Gly Phe Gln
        675                 680                 685

Glu Asp Pro Thr Glu Ile Lys Lys Thr Val Ala Val Asn Gly Ile Gly
    690                 695                 700

Thr Val Ile Leu Tyr Leu Ala Ser Asp Leu Lys Ser Phe Ala
705                 710                 715

<210> SEQ ID NO 4
<211> LENGTH: 1091
<212> TYPE: PRT
<213> ORGANISM: Klebsiella pneumonia

<400> SEQUENCE: 4

Met Leu Arg Tyr Thr Arg Asn Ala Leu Val Leu Gly Ser Leu Val Leu
1               5                   10                  15

Leu Ser Gly Cys Asp Asn Gly Ser Ser Ser Ser Ser Ser Ser Gly Asn
            20                  25                  30

Pro Asp Thr Pro Asp Asn Gln Asp Val Val Arg Leu Pro Asp Val
        35                  40                  45

Ala Val Pro Gly Glu Ala Val Thr Ala Val Glu Asn Gln Ala Val Ile
    50                  55                  60

His Leu Val Asp Ile Ala Gly Ile Thr Ser Ser Ser Ala Ala Asp Tyr
65                  70                  75                  80

Ser Ser Lys Asn Leu Tyr Leu Trp Asn Asn Glu Thr Cys Asp Ala Leu
                85                  90                  95

Ser Ala Pro Val Ala Asp Trp Asn Asp Val Ser Thr Thr Pro Ser Gly
            100                 105                 110
```

-continued

```
Ser Asp Lys Tyr Gly Pro Tyr Trp Val Ile Pro Leu Asn Lys Glu Ser
        115                 120                 125

Gly Cys Ile Asn Val Ile Val Arg Asp Gly Thr Asp Lys Leu Ile Asp
        130                 135                 140

Ser Asp Leu Arg Val Ala Phe Gly Asp Phe Thr Asp Arg Thr Val Ser
145                 150                 155                 160

Val Ile Ala Gly Asn Ser Ala Val Tyr Asp Ser Arg Ala Asp Ala Phe
                165                 170                 175

Arg Ala Ala Phe Gly Val Ala Leu Ala Glu Ala His Trp Val Asp Lys
            180                 185                 190

Asn Thr Leu Leu Trp Pro Gly Gly Gln Asp Lys Pro Ile Val Arg Leu
        195                 200                 205

Tyr Tyr Ser His Ser Ser Lys Val Ala Ala Asp Gly Glu Gly Lys Phe
    210                 215                 220

Thr Asp Arg Tyr Leu Lys Leu Thr Pro Thr Thr Val Ser Gln Gln Val
225                 230                 235                 240

Ser Met Arg Phe Pro His Leu Ser Ser Tyr Ala Ala Phe Lys Leu Pro
                245                 250                 255

Asp Asn Ala Asn Val Asp Glu Leu Leu Gln Gly Glu Thr Val Ala Ile
            260                 265                 270

Ala Ala Ala Glu Asp Gly Ile Leu Ile Ser Ala Thr Gln Val Gln Thr
        275                 280                 285

Ala Gly Val Leu Asp Asp Ala Tyr Ala Glu Ala Ala Glu Ala Leu Ser
    290                 295                 300

Tyr Gly Ala Gln Leu Ala Asp Gly Gly Val Thr Phe Arg Val Trp Ala
305                 310                 315                 320

Pro Thr Ala Gln Gln Val Asp Val Val Val Tyr Ser Ala Asp Lys Lys
                325                 330                 335

Val Ile Gly Ser His Pro Met Thr Arg Asp Ser Ala Ser Gly Ala Trp
            340                 345                 350

Ser Trp Gln Gly Gly Ser Asp Leu Lys Gly Ala Phe Tyr Arg Tyr Ala
        355                 360                 365

Met Thr Val Tyr His Pro Gln Ser Arg Lys Val Glu Gln Tyr Glu Val
    370                 375                 380

Thr Asp Pro Tyr Ala His Ser Leu Ser Thr Asn Ser Glu Tyr Ser Gln
385                 390                 395                 400

Val Val Asp Leu Asn Asp Ser Ala Leu Lys Pro Asp Gly Trp Asp Asn
                405                 410                 415

Leu Thr Met Pro His Ala Gln Lys Thr Lys Ala Asp Leu Ala Lys Met
            420                 425                 430

Thr Ile His Glu Ser His Ile Arg Asp Leu Ser Ala Trp Asp Gln Thr
        435                 440                 445

Val Pro Ala Glu Leu Arg Gly Lys Tyr Leu Ala Leu Thr Ala Gly Asp
    450                 455                 460

Ser Asn Met Val Gln His Leu Lys Thr Leu Ser Ala Ser Gly Val Thr
465                 470                 475                 480

His Val Glu Leu Leu Pro Val Phe Asp Leu Ala Thr Val Asn Glu Phe
                485                 490                 495

Ser Asp Lys Val Ala Asp Ile Gln Gln Pro Phe Ser Arg Leu Cys Glu
            500                 505                 510

Val Asn Ser Ala Val Lys Ser Ser Glu Phe Ala Gly Tyr Cys Asp Ser
        515                 520                 525

Gly Ser Thr Val Glu Glu Val Leu Asn Gln Leu Lys Gln Ser Asp Ser
```

-continued

```
            530                 535                 540
Gln Asp Asn Pro Gln Val Gln Ala Leu Asn Thr Leu Val Ala Gln Thr
545                 550                 555                 560

Asp Ser Tyr Asn Trp Gly Tyr Asp Pro Phe His Tyr Thr Val Pro Glu
                565                 570                 575

Gly Ser Tyr Ala Thr Asp Pro Glu Gly Thr Thr Arg Ile Lys Glu Phe
                580                 585                 590

Arg Thr Met Ile Gln Ala Ile Lys Gln Asp Leu Gly Met Asn Val Ile
                595                 600                 605

Met Asp Val Val Tyr Asn His Thr Asn Ala Ala Gly Pro Thr Asp Arg
610                 615                 620

Thr Ser Val Leu Asp Lys Ile Val Pro Trp Tyr Tyr Gln Arg Leu Asn
625                 630                 635                 640

Glu Thr Thr Gly Ser Val Glu Ser Ala Thr Cys Cys Ser Asp Ser Ala
                645                 650                 655

Pro Glu His Arg Met Phe Ala Lys Leu Ile Ala Asp Ser Leu Ala Val
                660                 665                 670

Trp Thr Thr Asp Tyr Lys Ile Asp Gly Phe Arg Phe Asp Leu Met Gly
                675                 680                 685

Tyr His Pro Lys Ala Gln Ile Leu Ser Ala Trp Glu Arg Ile Lys Ala
                690                 695                 700

Leu Asn Pro Asp Ile Tyr Phe Phe Gly Glu Gly Trp Asp Ser Asn Gln
705                 710                 715                 720

Ser Asp Arg Phe Glu Ile Ala Ser Gln Ile Asn Leu Lys Gly Thr Gly
                725                 730                 735

Ile Gly Thr Phe Ser Asp Arg Leu Arg Asp Ser Val Arg Gly Gly Gly
                740                 745                 750

Pro Phe Asp Ser Gly Asp Ala Leu Arg Gln Asn Gln Gly Ile Gly Ser
                755                 760                 765

Gly Ala Gly Val Leu Pro Asn Glu Leu Ala Ser Leu Ser Asp Asp Gln
                770                 775                 780

Val Arg His Leu Ala Asp Leu Thr Arg Leu Gly Met Ala Gly Asn Leu
785                 790                 795                 800

Ala Asp Phe Val Met Ile Asp Lys Asp Gly Ala Ala Lys Lys Gly Ser
                805                 810                 815

Glu Ile Asp Tyr Asn Gly Ala Pro Gly Gly Tyr Ala Ala Asp Pro Thr
                820                 825                 830

Glu Val Val Asn Tyr Val Ser Lys His Asp Asn Gln Thr Leu Trp Asp
                835                 840                 845

Met Ile Ser Tyr Lys Ala Ser Gln Glu Ala Asp Leu Ala Thr Arg Val
850                 855                 860

Arg Met Gln Ala Val Ser Leu Ala Thr Val Met Leu Gly Gln Gly Ile
865                 870                 875                 880

Ala Phe Asp Gln Gln Gly Ser Glu Leu Leu Arg Ser Lys Ser Phe Thr
                885                 890                 895

Arg Asp Ser Tyr Asp Ser Gly Asp Trp Phe Asn Arg Val Asp Tyr Ser
                900                 905                 910

Leu Gln Asp Asn Asn Tyr Asn Val Gly Met Pro Arg Ile Ser Asp Asp
                915                 920                 925

Gly Ser Asn Tyr Glu Val Ile Thr Arg Val Lys Glu Met Val Ala Thr
                930                 935                 940

Pro Gly Glu Ala Glu Leu Lys Gln Met Thr Ala Phe Tyr Gln Glu Leu
945                 950                 955                 960
```

```
Thr Glu Leu Arg Lys Ser Ser Pro Leu Phe Thr Leu Gly Asp Gly Ser
            965                 970                 975
Ala Val Met Lys Arg Val Asp Phe Arg Asn Thr Gly Ser Asp Gln Gln
            980                 985                 990
Ala Gly Leu Leu Val Met Thr Val Asp Asp Gly Met Lys Ala Gly Ala
            995                 1000                1005
Ser Leu Asp Ser Arg Leu Asp Gly Leu Val Ala Ile Asn Ala Ala
        1010                1015                1020
Pro Glu Ser Arg Thr Leu Asn Glu Phe Ala Gly Glu Thr Leu Gln Leu
1025                1030                1035                1040
Ser Ala Ile Gln Gln Thr Ala Gly Glu Asn Ser Leu Ala Asn Gly Val
            1045                1050                1055
Gln Ile Ala Ala Asp Gly Thr Val Thr Leu Pro Ala Trp Ser Val Ala
            1060                1065                1070
Val Leu Glu Leu Pro Gln Gly Glu Ala Gln Gly Ala Gly Leu Pro Val
        1075                1080                1085
Ser Ser Lys
        1090

<210> SEQ ID NO 5
<211> LENGTH: 6
<212> TYPE: PRT
<213> ORGANISM: Artificial Sequence
<220> FEATURE:
<223> OTHER INFORMATION: Unknown

<400> SEQUENCE: 5

Asp Val Val Ile Asn His
1               5

<210> SEQ ID NO 6
<211> LENGTH: 9
<212> TYPE: PRT
<213> ORGANISM: Artificial Sequence
<220> FEATURE:
<223> OTHER INFORMATION: Unknown

<400> SEQUENCE: 6

Gly Phe Arg Leu Asp Ala Ala Lys His
1               5

<210> SEQ ID NO 7
<211> LENGTH: 6
<212> TYPE: PRT
<213> ORGANISM: Artificial Sequence
<220> FEATURE:
<223> OTHER INFORMATION: Unknown

<400> SEQUENCE: 7

Phe Val Asp Val His Asp
1               5

<210> SEQ ID NO 8
<211> LENGTH: 5
<212> TYPE: PRT
<213> ORGANISM: Artificial Sequence
<220> FEATURE:
<223> OTHER INFORMATION: Unknown

<400> SEQUENCE: 8

Tyr Asn Trp Gly Tyr
1               5
```

```
<210> SEQ ID NO 9
<211> LENGTH: 4
<212> TYPE: PRT
<213> ORGANISM: Artificial Sequence
<220> FEATURE:
<223> OTHER INFORMATION: Unknown

<400> SEQUENCE: 9

Val Trp Ala Pro
1
```